US008697115B2

(12) United States Patent
Barrett-Reis et al.

(10) Patent No.: US 8,697,115 B2
(45) Date of Patent: *Apr. 15, 2014

(54) METHOD OF IMPROVING ANTIOXIDANT STATUS OF AN INFANT

(75) Inventors: Bridget Barrett-Reis, Dublin, OH (US); Marc L. Masor, Durango, CO (US)

(73) Assignee: Abbott Laboratories, Abbott Park, IL (US)

( * ) Notice: Subject to any disclaimer, the term of this patent is extended or adjusted under 35 U.S.C. 154(b) by 1746 days.

This patent is subject to a terminal disclaimer.

(21) Appl. No.: 11/391,798

(22) Filed: Mar. 29, 2006

(65) Prior Publication Data

US 2006/0171993 A1    Aug. 3, 2006

Related U.S. Application Data

(63) Continuation of application No. 10/112,823, filed on Mar. 29, 2002, now Pat. No. 7,090,862.

(51) Int. Cl.
*A61K 47/00* (2006.01)
*A61K 31/355* (2006.01)
*A61K 36/899* (2006.01)
*A61K 36/48* (2006.01)
*A61K 36/31* (2006.01)
*A61K 36/00* (2006.01)

(52) U.S. Cl.
USPC ........... 424/439; 514/458; 424/750; 424/757; 424/755; 424/769

(58) Field of Classification Search
USPC ......... 424/439, 441, 451, 464, 484, 489, 499, 424/727, 750, 755, 757, 769
See application file for complete search history.

(56) References Cited

U.S. PATENT DOCUMENTS

| | | |
|---|---|---|
| 4,710,387 A | 12/1987 | Uiterwaal et al. |
| 4,744,988 A | 5/1988 | Brox |
| 4,753,926 A | 6/1988 | Lucas et al. |
| 4,817,367 A | 4/1989 | Ishikawa et al. |
| 4,935,243 A | 6/1990 | Borkan et al. |
| 5,077,069 A | 12/1991 | Chang et al. |
| 5,179,122 A | 1/1993 | Greene et al. |
| 5,234,702 A | 8/1993 | Katz et al. |
| 5,260,077 A | 11/1993 | Carrick et al. |
| 5,290,605 A | 3/1994 | Shapira |
| 5,492,938 A | 2/1996 | Kyle et al. |
| 5,514,382 A | 5/1996 | Sultenfuss |
| 5,545,411 A | 8/1996 | Chancellor |
| 5,643,623 A | 7/1997 | Schmitz et al. |
| 5,660,842 A | 8/1997 | Petschow |
| 5,709,888 A | 1/1998 | Gil et al. |
| 6,207,187 B1 | 3/2001 | Clark et al. |
| 6,426,362 B1 | 7/2002 | Miller et al. |
| 7,090,862 B2 * | 8/2006 | Barrett-Reis et al. ......... 424/439 |
| 2002/0032234 A1 | 3/2002 | Hermelin et al. |

FOREIGN PATENT DOCUMENTS

WO    WO 00/65934 A1    11/2000
WO    WO 01/11991 A1    2/2001

OTHER PUBLICATIONS

Van Zoeren-Grobben, et al., "Vitamin E Status in Preterm Infants: Assessment by Plasma and Erythrocyte Vitamin E—Lipid Ratios and Hemolysis Tests" Journal of Pediatric Gastroenterology and Nutrition 26:73-79, Jan. 1998.
Mino, et al., "Red blood cell tocopherol concentrations in a normal population of Japanese children and premature infants in relation to the assessment of vitamin E status[1-3]", The American Journal of Clinical Nutrition 41: Mar. 1985, pp. 631-638.
McMurray, et al., "Influence of Extraction Techniques on Determination of α-Tocopherol in Animal Feedstuffs", J. Assoc. Off. Anal. Chem., vol. 63, No. 6, 1980.
Speek, et al., "Vitamin E Composition of Some Seed Oils as Determined by High-Performance Liquid Chromatography with Fluorometric Detection", Journal of Food Science, vol. 50, 1985.
Cort, et al., "Vitamin E Content of Feedstuffs Determined by High-Performance Liquid Chromatographic Fluorescence", J. Agric. Food Chem., 1983, 31, 1330-1333.
Acuff, et al., "Transport of deuterium-labeled tocopherols during pregnancy", Am J Clin Nutr 1998; 67: 459-64.
AOAC Official Methods of Analysis, 1995, Vitamins and Other Nutrients, Chapter 45, pp. 30-40.
Pryor, et al., "Noninvasive Measures of Oxidative Stress Status in Humans", Free Radical Biology & Medicine, vol. 10, pp. 177-184, 1991.
Morrow, et al., "The Isoprostanes: Current Knowledge and Directions for Future Research", Biochemical Pharmacology, vol. 51, pp. 1-9, 1996.
Committee on Nutrition American Academy of Pediatrics, Barness editor, *The Pediatric Nutrition Handbook*, Third Edition 1993, ch. 14, pp. 133-143.
Abstract, Stone, et al., "An Evaluation of Vitamin E Status of Infants Fed Formulas with Different Levels of Vitamin E", Pediatr Res Apr. 1999; 45 (4 Pt 2): 117A, Abstract 682.

* cited by examiner

*Primary Examiner* — Blessing M Fubara
(74) *Attorney, Agent, or Firm* — Calfee, Halter & Griswold LLP

(57) ABSTRACT

The present invention relates generally to a method of improving the antioxidant status of an infant. More particularly, the present invention relates to a method of improving the antioxidant status of an infant by administering a mixture of natural tocopherols. The natural tocopherol mixture is an effective blend of α- and γ-tocopherol. For ease of administration and improved taste, the mixture of natural tocopherols are typically delivered in vehicle which may be in the form, for example, of a tablet, capsule, liquid, and nutritional formula. The present invention also relates to a method of improving the antioxidant status of an infant by supplementing the lactating woman wherein the supplemented breast milk is fed to the infant. Additionally, the present invention relates to a method of improving the antioxidant status of a newborn infant by supplementing the pregnant woman.

7 Claims, No Drawings

METHOD OF IMPROVING ANTIOXIDANT STATUS OF AN INFANT

CROSS REFERENCE

This application is a continuation of U.S. patent application Ser. No. 10/112,823, which was filed on Mar. 29, 2002 now U.S. Pat. No. 7,090,862.

TECHNICAL FIELD

The present invention relates generally to a method of improving the antioxidant status of an infant. More particularly, the present invention relates to a method of improving the antioxidant status of an infant by administering a mixture of natural tocopherols. The tocopherol mixture is typically added to a delivery vehicle such as tablets, capsules, liquids, and nutritional formulas.

BACKGROUND

Vitamin E is a major antioxidant, effective in stabilizing unsaturated lipids in cell membranes against autooxidation. Furthermore, vitamin E scavenges free radicals produced by lipid peroxidation and by the normal activity of oxidative enzymes.

Vitamin E is a generic term for tocopherols and tocotrienols, which have saturated and unsaturated phytyl tails, respectively. The α-, β-, γ-, and δ-tocopherols and tocotrienols differ in the number and position of the methyl groups on the chroman ring (FIG. 1 and Table 1). The tocopherols can exist in a number of stereoisomeric forms depending on the chirality of the phytyl tail. Of these compounds RRR-α-tocopherol has the greatest biological activity and accounts for approximately 90% of the vitamin E found in tissues. Natural vitamin E (RRR-α-tocopherol) is a single stereoisomer whereas synthetic vitamin E (all-rac-α-tocopherol) is an equimolar mixture of eight isomers, only one of which is RRR-α-tocopherol. The other seven isomers of synthetic vitamin E have different molecular configurations, all with lower biological activity than RRR-α-tocopherol.

FIG. 1 Structure of Natural Tocopherols

TABLE 1

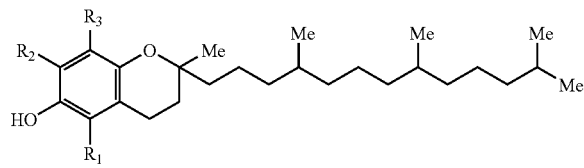

Structure of Natural Tocopherols

| Compound | $R_1$ | $R_2$ | $R_3$ |
|---|---|---|---|
| α-tocopherol | Me | Me | Me |
| β-tocopherol | Me | H | Me |
| γ-tocopherol | H | Me | Me |
| δ-tocopherol | H | H | Me |

Both free tocopherol and its acetate ester are water-insoluble, nonswelling amphiphiles, as are triglycerides and cholesterol. Thus, many of the factors and processes necessary for the absorption of dietary lipids are also required for absorption of tocopherols. These factors include: efficient emulsification, solubilization within mixed bile salt micells, uptake by the small intestinal cell (enterocyte), packaging within lipoprotein particles (chylomicrons) and secretion into the circulation via the lymphatic system.

Tocopherols must be emulsified and solubilized before their absorption across the brush-border membrane of the enterocyte. Emulsification begins in the stomach by predominantly mechanical forces that break up large emulsion particles into smaller particles. Within the small intestine chyme mixes with pancreatic and biliary secretions, which are necessary for the efficient absorption of tocopherol. Pancreatic lipase is necessary for the hydrolysis of triglyceride in the small intestine to monoglycerides and fatty acids. These lipolytic products, together with bile salts, form molecular aggregates known as mixed micelles that solubilize tocopherol. These mixed micelles are able to transport tocopherol across the unstirred water layer to the brush-border membrane of the enterocyte.

Once tocopherol has been solubilized within bile salt micelles and transported across the unstirred water layer, the micelle comes into contact with the absorptive brush-border membrane of the enterocyte. The uptake of tocopherol by the enterocyte takes place by passive diffusion. Thus, the process is non-saturable, noncarrier-mediated and unaffected by metabolic inhibitors and does not require energy. Within the enterocyte, tocopherol is incorporated into chylomicrons and secreted into the intracellular spaces and lymphatics and thus into the bloodstream.

Supplements of vitamin E are generally given in the form of α-tocopherol acetate in which the relative hydroxyl group of α-tocopherol is esterified, rendering the molecule more stable than the free form. Bile salts and the lipolytic products of triglycerides are necessary to solubilize the tocopheryl acetate before it can be hydrolyzed in the small intestinal lumen by pancreatic esterase. It is known that both α- and γ-tocopherols are absorbed by the enterocyte and secreted into the bloodstream within chylomicrons to a similar extent but that thereafter their handling is different. The liver, not the intestine, is capable of discriminating between these two tocopherols.

Vitamin E has been used as a "natural" antioxidant for the prevention of deterioration of food, cosmetic and pharmaceutical products that contain polyunsaturated fatty acids, which are susceptible to oxidation.

U.S. Pat. No. 5,234,702 to Katz discloses the incorporation of an antioxidant system of natural ingredients to minimize the oxidation of the fat system in a powdered nutritional product. The antioxidant system is made up of from 400-1200 ppm of ascorbyl palmitate, 6-20 ppm beta-carotene, and at least 1000 ppm of citrate, the ppm of ascorbyl palmitate and beta carotene being expressed with respect to said oil blend when the oil blend is in a liquid state, and the ppm of citrate being expressed with respect to the total weight of the product when the product is in a powdered form. The antioxidant system may also contain from 200-1200 ppm of mixed tocopherols, the ppm of the mixed tocopherols being expressed with respect to the oil blend when the oil blend is in a liquid state. The mixed tocopherols contain a mixture of alpha, beta, gamma, and delta tocopherol.

Additional commercial uses of Vitamin E include incorporation of antioxidant packages into foods designed to alleviate the effects of oxidative stress.

U.S. Pat. No. 5,643,623 to Schmitz, et al. describes a health food product with a blend of antioxidant components that enhance in vivo oxidant defense indices, and reduce in vivo oxidant stress and damage resulting from intense exercise. The antioxidant blend is a mixture of at least two antioxidants selected from curcumin, all-trans beta-carotene, cis beta-carotene, all-trans alpha-carotene, cis alpha-carotene, all-trans lycopene, cis lycopenes, all-trans gamma-carotene, cis gamma-carotene, zeta-carotene, phytofluene, phytoene, vitamin C and vitamin E. The antioxidants are concentrated in a core or discrete portion within a food product to provide protection from heat, light and oxygen and also to avoid disadvantageous coloration of the food product by the antioxidants. Preferably, the antioxidants are localized in a lipid-based carrier within a food product to promote absorption and digestion of the carotenoid blend and curcumin. The patent is silent as to the form or ratios of tocopherols to be utilized in the antioxidant blend.

U.S. Pat. No. 5,290,605 to Shapira discloses a nutritional soft drink for protecting against the danger of exposure to UV light comprising a mixture of carotenoids, optionally together with vitamin C and/or vitamin E and/or other physiologically acceptable antioxidants in an amount which does not exceed 10 vitamin ARDA equivalents of provitamin A per liter of drink.

Vitamin E is also a common component of vitamin and mineral supplements designed for different life stages and genders, which allow each group to maintain their present health and positively influence their future health.

U.S. Pat. No. 5,514,382 to Sultenfuss describes a daily vitamin and mineral supplement for women. The supplement contains vitamin A, beta-carotene, niacin, riboflavin, pantothenic acid, pyridoxine, cyanocobalamin, biotin, para-aminobenzoic acid, inositol, choline, vitamin C, vitamin D, vitamin E, vitamin K, boron, calcium, chromium, copper, iodine, iron, magnesium, manganese, molybdenum, selenium, zinc and bioflavonoid. For women up to 40 years of age, iron is included. For women over 40 years of age, iron is optionally included. The α-tocopherol form of vitamin E is the compound utilized in the supplement. In the preferred embodiment, for women up to 40 years of age and women over 40 years of age, a dosage between about 400 to about 800 milligrams of vitamin E is recommended. In the preferred embodiment, 800 milligrams of α-tocopherol is used.

International application, WO 01/11991 A1, to Warner Chilcott Laboratories describes a chewable prenatal vitamin/mineral supplement. The supplement contains a combination of vitamins and minerals such as: folic acid, beta-carotene, vitamin $B_1$, $B_2$, $B_6$, $B_{12}$, D, E, C, niacin and iron. Preferably the supplement contains 1 to 20 IU of vitamin E acetate.

Furthermore, several prenatal supplements are available which provide pregnant women with varying amounts of vitamins and minerals. The Physicians' Desk Reference (54th Ed., 2000) describes various vitamin and mineral supplements for use by pregnant women. For example, NESTABS® CBF tablets, prenatal formula, available from The Fielding Company, Maryland Heights, Mo., contains 4,000 I.U. of vitamin A, 400 I.U. of vitamin D, 30 I.U. of vitamin E, 120 mg of vitamin C, 1 mg of folic acid, 3 mg of thiamine, 3 mg of riboflavin, 20 mg of niacinamide, 3 mg of pyridoxine, 8 mcg of vitamin $B_{12}$, 200 mg of calcium, 150 mcg of iodine, 15 mg of zinc, and 50 mg of iron per dose. NESTABS® are expressly formulated for use during pregnancy and lactation and are available only in tablet form.

MATERNA® prenatal vitamin and mineral formula, available from Lederle Laboratories, Pearl River, N.Y., Contains 5,000 I.U. of vitamin A, 400 I.U. of vitamin D, 30 I.U. of vitamin E (dl-alpha-tocopheryl acetate), 120 mg of vitamin C, 1 mg of folic acid, 3 mg of vitamin $B_1$, 3.4 mg of vitamin $B_2$, 10 mg of vitamin $B_6$, 20 mg of niacinamide, 12 mcg of vitamin $B_{12}$, 30 mcg of biotin, 10 mg of pantothenic acid, 200 mg of calcium, 150 mcg of iodine, 27 mg of iron, 25 mg of magnesium, 2 mg of copper, 25 mg of zinc, 25 mcg of chromium, 25 mcg of molybdenum, 5 mg of manganese, and 20 mcg of selenium per dose. MATERNA® is designed to provide, in one tablet daily, vitamin and minerals supplementation prior to conception, throughout pregnancy and during the postnatal period for both lactating and nonlactating mothers and is available in tablet form only.

ENFAMIL® NATALINS® RX multivitamin and multimineral supplements, available from Mead Johnson Nutritionals, Evansville, Ind., provide 4000 I.U. of vitamin A, 80 mg of vitamin C, 400 I.U. of vitamin D, 15 I.U. of vitamin E, 1.5 mg of thiamin, 1.6 mg of riboflavin, 17 mg niacin, 4 mg of vitamin $B_6$, 1 mg of folic acid, 2.5 mcg of vitamin $B_{12}$, 30 mcg of biotin, 7 mg of pantothenic acid, 200 mg of calcium, 54 mg of iron, 100 mg magnesium, 25 mg of zinc, and 3 mg of copper per dose (two tablets daily). ENFAMIL® NATALINS® RX are to supplement the diet during pregnancy or lactation and are available only in tablet form.

PRENATE® ULTRA™ prenatal vitamins, available from Sanofi Pharmaceuticals, New York, N.Y., contain 90 mg of elemental iron, 150 mcg of iodine, 200 mg of calcium, 2 mg of copper, 25 mg of zinc, 1 mg of folic acid, 2700 I.U. of vitamin A, 400 I.U. of vitamin D, 30 I.U. of vitamin E (dl-alpha-tocopheryl acetate), 120 mg of vitamin C, 3 mg of vitamin $B.sub_1$, 3.4 mg of vitamin $B_2$, 20 mg of vitamin $B_6$, 12 mcg of vitamin $B_{12}$, 20 mg of niacinamide, and 50 mg of docusate sodium per dose. PRENATE® ULTRA™ is indicated for use in improving the nutritional status in women throughout pregnancy and in the postnatal period for both lactating and nonlactating mothers and is only available in tablet form.

NIFEREX®-PN tablets, available from Schwarz Pharma, Inc., Milwaukee, Wis., contains 60 mg of iron, 1 mg of folic acid, 50 mg of vitamin C, 3 mcg of vitamin $B_{12}$, 4,000 I.U. of vitamin A, 400 I.U. of vitamin D, 2.43 mg of vitamin $B_1$, 3 mg of vitamin $B_2$, 1.64 mg of vitamin $B_6$, 10 mg of niacinamide, 125 mg of calcium, and 18 mg of zinc per dose (one tablet). NIFEREX®-PN is indicated for prevention and/or treatment of dietary vitamin and mineral deficiencies associated with pregnancy and lactation and is only available in tablet form.

NIFEREX®-PN FORTE tablets, available from Schwarz Pharma, Inc., Milwaukee, Wis., contains 5,000 I.U. of vitamin A, 400 I.U. of vitamin D, 30 I.U. of vitamin E (dl-alpha-tocopheryl acetate), 80 mg of vitamin C, 1 mg of folic acid, 3 mg of vitamin $B_1$, 3.4 mg of vitamin $B_2$, 4 mg of vitamin $B_6$, 20 mg of niacinamide, 12 mcg of vitamin $B_{12}$, 250 mg of calcium, 200 mcg of iodine, 10 mg of magnesium, 2 mg of copper, and 25 mg of zinc per dose. NIFEREX®-PN FORTE is indicated for prevention and/or treatment of dietary vitamin and mineral deficiencies associated with pregnancy and lactation and is only available in tablet form.

PRECARE® prenatal multi-vitamin/mineral film coated caplet, available from UCB Pharma, Inc., Smyrna, Ga., contains 50 mg of vitamin C, 250 mg of calcium, 40 mg of iron, 6 mcg of vitamin D, 3.5 mg of vitamin E (dl-alpha-tocopheryl acetate), 2 mg of vitamin $B_6$, 1 mg of folic acid, 50 mg of magnesium, 15 mg of zinc and 2 mg of copper per dose (one caplet). PRECARE® is indicated to provide vitamin and mineral supplementation throughout pregnancy and during the postnatal period-for both lactating and nonlactating mothers and is available only in caplet form.

NATAFORT® prenatal multivitamin, available from Warner Chilcott, Rockaway, N.J., contains 1,000 I.U. vitamin A, 400 I.U. of vitamin D, 11 I.U. of vitamin E (dl-alpha-tocopheryl acetate), 120 mg of vitamin C, 1 mg of folic acid, 2 mg of thiamine, 3 mg of riboflavin, 20 mg of niacinamide, 10 mg of vitamin $B_6$, 12 mcg of vitamin $B_{12}$, and 60 mg of iron per dose (one tablet daily). NATAFORT® is designed to provide vitamin and mineral supplementation throughout pregnancy and during the postnatal period, for both the lactating and non-lactating mother and is only available in tablet form.

VI-DAYLIN® multivitamin supplement, available from Ross Products, Division of Abbott Laboratories, Columbus, Ohio contains 1350 I.U. vitamin A, 31.5 mg vitamin C, 360 I.U. vitamin D, 4.5 I.U. vitamin E (d-alpha-tocopheryl polyethylene glycol 1000 succinate), 0.401 mg thiamin, 0.45 mg riboflavin, 7.2 mg niacin, 0.36 mg vitamin $B_6$ and 1.35 mcg $B_{12}$ per dose (1 ml). VI-DAYLIN® is designed to provide vitamin and mineral supplementation to an infant.

VI-DAYLIN® multivitamin supplement with iron, available from Ross Products, Division of Abbott Laboratories, Columbus, Ohio contains 1350 I.U. vitamin A, 31.5 mg vitamin C, 360 I.U. vitamin D, 4.5 I.U. vitamin E (d-alpha-tocopheryl polyethylene glycol 1000 succinate), 0.446 mg thiamin, 0.45 mg riboflavin, 7.2 mg niacin, 0.36 mg vitamin $B_6$ and 9 mg iron per dose (1 ml). VI-DAYLIN® is designed to provide vitamin and mineral supplementation to an infant.

However, none of the above formulations above provide women or infant with the proper ratios of vitamin E necessary to optimize infant antioxidant status. Further, the prenatal nutritional supplements do not contain the natural form of vitamin E (RRR-α-tocopherol).

In addition to dietary supplements, vitamin E is commonly fortified in adult and infant nutritionals.

Over the last 50 years, the importance of infant formulas has evolved from meeting the nutritional needs of infants during the first year of life to optimizing health throughout life. Commercial infant formulas are fortified with vitamin E to meet the minimum levels recommended by AAP/CON (Pediatric Nutrition Handbook, Ed 3. Elk Grove Village, Ill: American Academy of Pediatrics, 1993). Vitamin E is also a component of many of the oil sources utilized in infant formulas. Table 2 lists the vitamin E content and the sources of oil for various commercially available milk based and soy based infant formulas.

As described in Table 2, commercially available infant formulas that contain synthetic all-rac-α-tocopherol acetate are typically fortified at higher levels than the infant formulas that contain natural RRR-α-tocopherol acetate. These fortification levels fall within the range of total vitamin E content of human milk. In general, total vitamin E content of human colostrum is high (average content ranges from 6.8-23 mg/L). The vitamin E concentration decreases in transitional milk, sampled at 6-10 days, and further decreases in mature milk. The range of vitamin E concentrations in mature human milk after approximately 30 days of lactation varies from 1.8 mg/L to approximately 9 mg/L.

As discussed above, the discrimination between synthetic and natural forms of vitamin E in the adult appears not to occur during absorption, but rather as a post-absorptive phenomenon in the liver involving a cytosolic tocopherol binding protein that selectively transfers RRR-α-tocopherol from the endoplasmic reticulum to newly secreted very low density lipoproteins (VLDL). It has been shown in adults that VLDL secreted by the liver is enriched (4-fold) in RRR-α-tocopherol over all-rac-α-tocopherol. Natural vitamin E is also preferentially taken up by plasma and RBCs in adults. It is also known that there is a preferential urinary excretion of all-rac-α-tocopherol over that of RRR-α-tocopherol. However, it is not known if an infant can discriminate between synthetic and natural forms of vitamin E. It is well established that vitamin E functions as an in vivo antioxidant, protecting lipids against peroxidative damage and it is known that red blood cells (RBCs) from newborns are more sensitive to in vitro oxidative stress than adult RBCs. Most of the intracellular hemoglobin (HB) in neonatal RBCs is HBF, which has a stronger tendency to denature and oxidize than HbA. Denatured and oxidized Hb is a potent catalyst for lipid peroxidation. Further, exposure to free radicals places the preterm infant at risk for diseases of prematurity including intaventricular hemorrhage, retinopathy of prematurity, bronchopulmonary dysplasia and nectrotizing enterocolitis.

TABLE 2

Vitamin E content and oil sources for various commercial infant formulas

| Formula | Vitamin E (Vitamin E source) | Oil sources |
| --- | --- | --- |
| Milk Based Formulas | | |
| Similac ® | 1.5 IU/100 kcal (RRR-α-tocopheryl acetate) | High oleic safflower, soybean, and coconut oils |
| Similac ® PM 60/40 | 2.5 IU/100 kcal (All-rac-α-tocopherol acetate) | Corn, soybean and coconut oils |
| Similac NeoSure ™ | 3.6 IU/100 kcal (All-rac-α-tocopherol acetate) | High oleic safflower, soybean, coconut and MCT oils |
| Similac ® Special Cares ® | 4.0 IU/100 kcal (All-rac-α-tocopherol acetate) | Soybean, coconut and MCT oils |
| Enfamil ® | 2.0 IU/100 kcal (All-rac-α-tocopherol acetate) | Soy, Coconut, High-Oleic Sunflower and Palm Olein Oils |
| Soy Based Formulas | | |
| Isomil ® | 1.5 IU/100 kcal (RRR-α-tocopheryl acetate) | High-oleic safflower, soybean and coconut oils |
| ProSobee ® | 2.0 IU/100 kcal (All-rac-α-tocopherol acetate) | Palm Olein, Soy, Coconut, and High-Oleic Sunflower Oils |

ProSobee ® and Enfamil ® data from Mead Johnson & Company, Evansville, IN, product literature
Similac ® and Isomil ® data from Ross Products Division of Abbott Laboratories, Columbus, OH, product literature It would therefore be desirable to deliver a specifically designed preferential γ- to α-tocopherol ratio that will support the antioxidant status of the infant. The compositions of the present inventive subject matter overcome the deficiencies of currently-available nutritional supplements by providing formulations which are specifically tailored for 1) pregnant and lactating women and 2) infants which optimize infant antioxidant status.

SUMMARY OF THE INVENTION

The present invention relates generally to a method of improving the antioxidant status of an infant. More particularly, the present invention relates to a method of improving the antioxidant status of an infant by administering a mixture of natural tocopherols, optionally in combination with various vitamins, minerals and macronutrients. The natural tocopherol mixture is an effective blend of γ- and α-tocopherol. For ease of administration and improved organoleptics, the mixture of natural tocopherols are typically delivered in an oral dosage form. The present invention also relates to a method of improving the antioxidant status of an infant by supplementing the lactating woman wherein the supplemented breast milk is delivered to the infant. Additionally, the present invention relates to a method of improving the antioxidant status of a newborn infant by supplementing the pregnant woman.

The inventors discovered that infants discriminate between RRR-α-tocopherol (natural vitamin E) and the other seven stereoisomers present in synthetic vitamin E. Further, the inventors, unexpectantly, discovered that infants fed formulas supplemented with higher levels of natural vitamin E do not experience a better antioxidant status when compared to infants fed the same formula supplemented with lower levels of natural vitamin E. In fact, the infants fed the formula with lower levels of natural vitamin E have a better antioxidant status. It appears that the higher intake of RRR-α-tocopherol negatively impacts γ-tocopherol concentrations and it is this γ- to α-tocopherol ratio that is crucial for improved antioxidant status in infants.

The instant invention is directed to a method of improving antioxidant status of an infant by administering the required amount of vitamin E in a γ- to α-tocopherol ratio from about 1:2 γ- to α-tocopherol to about 10:1 γ- to α-tocopherol, preferably from about 1.0:1.6 γ- to α-tocopherol to about 6:1 γ- to α-tocopherol, more preferable from about 1.0:1.4 γ- to α-tocopherol to about 2:1 γ- to α-tocopherol. In certain embodiments, the vitamin E is administered in a γ- to α-tocopherol ratio from about 1:2 γ- to α-tocopherol to about 6:1 γ- to α-tocopherol.

Successful breast-feeding requires that the mother maintain good nutrition and adequate rest. A good, nutritional diet is needed to support the stamina that nursing an infant requires. Beyond this, however, a woman must consume a nutrient-rich diet to produce nutrient-rich milk.

A healthy nursing mother generally makes about 25 ounces of milk each day. To produce this milk, the mother needs to consume 650 kilocalories above what she would normally require for herself. Women are advised to eat about 500 kilocalories worth of extra food and let the extra fat left over from pregnancy provide the rest. Woman may not consume enough food for many reasons, including the desire to lose all of the weight gained during pregnancy. But restricting food and energy in this fashion will result in breast milk that is lacking in nutrients, low quantities of breast milk or, in the worse case scenario, no breast milk at all.

According to the medical literature, a nursing mother should eat foods high in nutrients and drink plenty of fluid. Nutritional deprivation in the mother generally reduces the quantity, more so than the quality, of the milk. So while woman can produce milk with sufficient protein, carbohydrate, fat and minerals even if their own intake is insufficient, the quality of the breast milk is maintained at the expense of the mother's own nutrient repositories. Moreover, quantities of particular vitamins, such as B6, B12, A and D, in breast milk will actually decline in response to inadequate intakes by the mother. The inventors have also discovered that the secretion of vitamin E into breast milk discriminates between natural and synthetic vitamin E carried in plasma lipoproteins.

The invention is also directed to a method of promoting antioxidant status of a breastfed infant by administering to a lactating woman the required amount of vitamin E a γ- to α-tocopherol ratio from about 1:2 γ- to α-tocopherol to about 10:1 γ- to α-tocopherol, preferably from about 1.0:1.6 γ- to α-tocopherol to about 6:1 γ- to α-tocopherol, more preferable from about 1.0:1.4 γ- to α-tocopherol to about 2:1 γ- to α-tocopherol. In certain embodiments, the vitamin E is administered in a γ- to α-tocopherol ratio from about 1:2 γ- to α-tocopherol to about 6:1 γ- to α-tocopherol.

Prior to the production of nutrient-rich milk, a good nutritional diet is also needed to support fetal development. During this intense period of physiologic growth and development, the mother's diet must supply all the critical nutritional demands of the fetus and her own changing body.

According to the National Research Council (NRC), a pregnant woman should eat foods high in nutrients and drink plenty of fluid. Sufficient kilocalories must be available to supply the increased energy and nutrient demands, including the development of maternal fat storage and fetal fat storage to ensure an optimal newborn size for survival and to spare protein for tissue building. The current RDA standard recommends an additional amount of energy, 300 kcal during the second and third trimesters of rapid growth, which is about a 10% to 15% increase over the mother's general pre-pregnant need. While fetal development will occur even if nutrient intake is insufficient, the growth is maintained at the expense of the mother's own nutrient repositories. In addition to the increased energy requirement, increased levels of particular vitamins and minerals are also required during pregnancy. These vitamin include the B complex vitamins, vitamin A, C, D, and the minerals calcium and iron. It is also known that the human placenta delivers natural vitamin E to the fetus significantly more efficiently than synthetic vitamin E.

The invention is also directed to a method of promoting antioxidant status of a newborn infant by administering to a pregnant woman the required amount of vitamin E in a γ- to α-tocopherol ratio from about 1:2 γ- to α-tocopherol to about 10:1 γ- to α-tocopherol, preferably from about 1.0:1.6 γ- to α-tocopherol to about 6:1 γ- to α-tocopherol, more preferable from about 1.0:1.4 γ- to α-tocopherol to about 2:1 γ- to α-tocopherol. In certain embodiments, the vitamin E is administered in a γ- to α-tocopherol ratio from about 1:2 γ- to α-tocopherol to about 6:1 γ- to α-tocopherol.

The γ- to α-tocopherol ratio may be delivered in a vehicle which may be in the form of, for example, chewable tablet, quick dissolve tablet, an effervescent tablet, a hard gelatin capsule, a soft gelatin capsule, reconstitutable particles, microparticles, a suspension, an elixir, a caplet, a fortified food, pudding, yogurts, gelatin, cereal, infant nutritional formulas, adult nutritional formulas and combinations thereof.

The γ- and α-tocopherol sources may be isolated tocopherol components, oils rich in γ- and/or α-tocopherol and mixtures thereof.

DETAILED DESCRIPTION OF THE INVENTION

As used herein:

The term "RTF" refers to a formula that may be consumed without requiring additional compositional changes prior to consumption. For example, a RTF infant formula may be fed directly to the infant without having to mix water or another fluid; such is the case with powdered formulas or concentrated forms of liquid products.

The "numerical ranges" cited herein should be construed as encompassing any subrange. For example, a range of from about 2 to about 8 would encompass the subrange of from about 3 to about 7.

The term "breastfed infant" refers to an infant fed human derived breast milk. The infant may be actively breastfed, may receive expressed human milk from the mother or from milk pools, which are often located in hospitals.

The term "vehicle or carrier" and "oral dosage form" includes but is not limited to the FDA statutory food categories: conventional foods, foods for special dietary uses, dietary supplements and medical foods; and chewable tablet, quick dissolve tablet, an effervescent tablet, a hard gelatin capsule, a soft gelatin capsule, reconstitutable particles, microparticles, a suspension, an elixir, a caplet, a fortified food, pudding, yogurts, gelatin, cereal, adult nutritionals, infant nutritionals and combinations thereof. "Foods for special dietary uses" are intended to supply a special dietary need that exists by reason of a physical, physiological, pathological condition by supplying nutrients to supplement the diet or as the sole item of the diet. A "dietary supplement" is a product intended to supplement the diet by ingestion in tablet, capsule or liquid form and is not represented for use as a conventional food or as a sole item of a meal or the diet. A "medical food" is a food which is formulated to be consumed or administered enterally under the supervision of a physician and which is intended for the specific dietary management of a disease or condition for which distinctive nutritional requirements, based on recognized scientific principles, are established by medical evaluation.

The term "Dietary Reference Intakes" or "DRI" refers to a generic term for a set of nutrient reference values that includes Estimated Average Requirement (EAR), Recommended Dietary Allowance (RDA), Adequate Intake (AI) and Tolerable Upper Intake Level (UL). These reference values have been developed for life stage and gender groups in a joint U.S.-Canadian activity by the Standing Committee on the Scientific Evaluation of Dietary Reference Intakes of the Food and Nutrition Board (FNB), Institute of Medicine, National Academy of Sciences. The FNB has issued a series of DRI books with recommendations for various groupings of nutrients, such as, Dietary Reference Intakes for Calcium, Phosphorus, Magnesium, Vitamin D and Fluoride (National Academy Press, Washington D.C., 1997), Dietary Reference Intakes for Thiamin, Riboflavin, Niacin, Vitamin $B_6$, Folate, Vitamin $B_{12}$, Pantothenic Acid, Biotin and Choline (National Academy Press, Washington D.C., 2000), Dietary Reference Intakes for Vitamin A, Vitamin K, Arsenic, Boron, Chromium, Copper, Iodine, Iron, Manganese, Molybdenum, Nickel, Silicon, Vanadium and Zinc (National Academy Press, Washington D.C., 2001), Dietary Reference Intakes for Vitamin C, Vitamin E, Selenium and Carotenoids (National Academy Press, Washington D.C., 2000), The term "the required amount of vitamin E" relates to the prenatal relevant amounts of vitamin E, the lactating relevant amounts of vitamin E and/or the vitamin E requirement for infants as recommended by the Food and Nutrition Board (FNB).

The term "prenatal relevant amount" of vitamins and minerals relates to the Food and Nutrition Board's recommended dietary allowance (RDA) or the adequate intake (AI) when the RDA is not identified for pregnant women.

The term "lactating relevant amount" of vitamins and minerals relates to the Food and Nutrition Board's recommended dietary allowance (RDA) or the adequate intake (AI) when the RDA is not identified for pregnant women.

The term "natural tocopherol ratio", "γ- to α-tocopherol ratio", "vitamin E" and "natural vitamin E", "mixture of natural tocopherols" refer to the RRR-α-tocopherol, RRR-α-tocopherol acetate, RRR-α-tocopherol succinate and RRR-γ-tocopherol, RRR-γ-tocopherol acetate, RRR-γ-tocopherol succinate forms and derivatives thereof.

Vitamin E Analysis

The methodology for determining vitamin E has progressed from biological methods (rat fertility tests) to chemical methods (for example, gold chloride method, nitric acid method, cerimetric titration method, ferric chloride-dipyridyl method) to paper and thin-layer chromatography methods. Modern methods for the analysis of the tocopherols (both tocols and tocotrienols) are typically based either on gas-liquid chromatography (GLC) or high-performance liquid chromatography (HPLC). Based on the tocopherol isomer and the characteristics of the item to be tested, one knowledgeable in the art would be able to select an appropriate analytical method from the numerous methods in the literature. In addition to the analytical methods utilized in Example I, Cort, et al. (Journal of Agricultural Food Chemistry, 31:1330-1333, 1983), Speek, et al. (Journal of Food Science, 50: 121-124, 1985), McMurray, et al. (Journal of the Association of Official Analytical Chemists, 63:1258-1261, 1980) and Cunniff (Official Methods of Analysis of AOAC International, $16^{th}$ ed, $3^{rd}$ rev, chapter 45, 30-40, 1997) describe typical tocopherol analytical methods found in the literature.

Oxidative Stress Status Analysis

A variety of methods for the measurement of oxidative stress have been proposed in the literature. One of the problems in measuring oxidative stress is that active oxygen species and free radicals are so reactive and short lived that they are difficult to measure directly. For this reason, most methodologies measure the defense indices and/or putative products of oxidative stress. Typically, measurements of oxidative stress in humans include noninvasive methods, generally limiting the protocols to those sampling urine, blood plasma or exhaled gases, although needle biopsy of adipose tissue for vitamin E status or synovial fluid for peroxides has been utilized. Pryor et al. (Free Radical Biology & Medicine, 10: 177-184, 1991) provides a review and references of many analytical approaches to measure oxidative stress status in a human and is incorporated herein by reference. Additionally, specific methods for red blood cell tocopherols, plasma cholesterol and triglycerides may be found in Example I. Table 3 lists examples of non-enzymatic and enzymatic oxidant defense indices as well as products of oxidative stress that have been utilized to evaluate oxidative status.

TABLE 3

Measures of Oxidative Stress Status in Humans

| | |
|---|---|
| 1. Measurement of oxidant defense indices: | non-enzymatic oxidant defense indices present in serum, such as glucose, pyruvate, uric acid, ascorbic acid, bilirubin, carotenoids, vitamin E, lycopene, lutein, and ubiquinol-10<br>enzymatic oxidant defense indices present in serum, such as intracellular superoxide dismutase, catalase, glutathione peroxidase, glutathione reductase, phospholipid hydroperoxide glutathione peroxidase and glutathione S-transferase; and extracellular superoxide dismutase |
| 2. Measurement of oxidative stress: | low density lipoprotein susceptibility to peroxidation<br>carbonyls in expired breath<br>protein carbonyls in serum<br>serum and urinary lipoperoxides<br>formation of DNA cross-link products<br>non-enzymatic prostanoids |
| 3. Measurement of oxidative stress via inflammatory related processes: | thromboxane A2 production/platelet aggregation<br>serum and urinary prostacyclin<br>eicosinoid synthesis<br>platelet lipoxygenase |

As described above, various methods have been identified to quantify products of free radical-induced lipid peroxidation as a means to assess oxidant injury. These include measurements of malondialdehyde (MDA), lipid hydroperoxides, conjugated dienes, and short-chain alkanes, among others. Morrow et al. (Biochemical Pharmacology, 51, 1-9, 1996) discovered that the measurement of isoprostanes could provide a reliable measure of oxidant injury not only in vitro but also more importantly in vivo. It is generally accepted that the quantification of $F_2$-isoprostanes, in particular 8-epi-prostaglandin $F_{2\alpha}$ (8-epi-$PF_{2\alpha}$), which are some of the most abundant forms of isoprostanes, represents a reliable and useful approach to assess lipid peroxidation and oxidant stress in vivo. These unique prostaglandin-like compounds are produced in vivo by a noncyclooxygenase mechanism involving peroxidation of arachidonic acid. $F_2$-isoprostanes are very stable molecules and can be detected in measurable quantities esterified in all body tissues and in free form in every biological fluid tested including plasma, urine, bile, gastric juice, synovial fluid and cerebrospinal fluid. Thus $F_2$-isoprostanes is the currently preferred marker of in vivo oxidant injury.

Food Chemicals Codex (FCC IV) Nomenclature

The FCC (4th ed. Washington, D.C.: National Academy Press, 1996, 417-424) sets standards for food-grade chemicals among which is vitamin E. In this compendium, the various vitamin E analogs are identified by their trivial names (see Table 4). The unit of measurement is milligrams of the vitamin E analog per gram of total tocopherols. Although IUs are no longer recognized, many fortified foods and supplements still retain this terminology. Label claims in terms of International Units (IU) should be based on the relative vitamin E isomer activities listed in Table 4 below.

TABLE 4

Vitamin E Activity

| Isomer | Activity (IU/mg)* |
|---|---|
| d,l-α-tocopherol | 1.1 |
| d,l-α-tocopherol acetate | 1.0 |
| d-α-tocopherol | 1.49 |
| d-α-tocopherol acetate | 1.36 |

TABLE 4-continued

Vitamin E Activity

| Isomer | Activity (IU/mg)* |
|---|---|
| d-α-tocopherol acid succinate | 1.21 |
| d,l-α-tocopherol acid succinate | 0.89 |

*Food Chemicals Codex effective Jul. 1, 1996

Association of Official Analytical Chemists (AOAC) Nomenclature

The Association of Official Analytical Chemists (AOAC; 16th ed. 1997; 2: chap. 45, p. 30) states that the "term vitamin E should be used as generic descriptor for all tocol- and tocotrienol derivatives" that exhibit biological activity of α-tocopherol. Consequently the term "tocopherols" is not only synonymous with the term "vitamin E" but is a generic descriptor for all methyl tocols. Under this set of nomenclature rules, α-tocopherol is a trivial name without sterochemical designation (Table 5). Table 5 correlates the nomenclature for vitamin E.

TABLE 5

Nomenclature for Vitamin E

| | AOAC* | |
|---|---|---|
| Trivial Name | Name | Designated Name |
| α-tocopherol | 5,7,8-trimethyltocol | — |
| d-α-tocopherol | 2R,4'R,8'R-α-tocopherol | RRR-α-tocopherol |
| l-α-tocopherol | 2S,4'R,8'R-α-tocopherol | 2-Epi-α-tocopherol |
| d,l-α-tocopherol (totally synthetic) | 2DL,4'DL,8'DL-α-tocopherol | All-rac-α-tocopherol |
| d,l-α-tocopherol (synthesis from natural phytol) | — | 2-Ambo-α-tocopherol |
| β-tocopherol | — | 5,8-Dimethyltocol |
| γ-tocopherol | — | 7,8-Dimethyltocol |
| δ-tocopherol | — | 8-Methyltocol |
| Tocotrienol | 2-Methyl-2-(4',8',12'-trimethylthrideca-3',7',11'-tnenyl) ehroman-6-ol | — |

*Association of Official Analytical Chemists current through March 1997 Supplement Food and Nutrition Board (FNB) Dietary Requirements for Vitamin E The Food and Nutrition Board (FNB) has issued a new edition of DRI: Dietary Reference Intakes for Vitamin C, Vitamin E, Selenium, and Carotenoids (Washington, D.C.: National Academy of Sciences. 2000), in which the occurrence, adequate intake and biological activity of vitamin E are summarized in detail. It is emphasized that there are two groups of compounds found in plant materials that have vitamin E biological activity, that is, tocopherols and tocotrienols. The tocopherols are characterized by a substituted, hydroxyl Ted ring system (criminal ring) with a long, saturated (phenyl) side chain. Tocotrienols differ from tocopherols only in that they have an unsaturated side chain. The naturally occurring tocopherols include α-, β-, γ-, and δ-tocopherols. These various forms are not interconvertible in the human and thus do not behave the same metabolically. The FNB limits the vitamin E activity of α-tocopherol to that available from the naturally occurring form (RRR-) and the other three synthetic 2R-stereoisomer forms (RSR-, RRS-, and RSS-) of α-tocopherol for purposes of establishing the human requirement for vitamin E. Other natural occurring forms of vitamin E (β-, γ-, δ-tocopherols and the tocotrienols) do not contribute toward meeting the vitamin E requirement because, although absorbed, there are not converted to α-tocopherol by humans and are recognized poorly by the α-tocopherol transfer protein in the liver.

Based on a review of the data by the FNB, the 2R-stereoisomeric forms of α-tocopherol (RSR-, RRS-, and RSS-) were used to estimate the vitamin E requirement. Thus, the Estimated Average Requirements (ERAs), Recommended Dietary Allowances (RDAs), and Adequate Intakes (AIs) that are listed below apply only to intake of the 2R-stereoisomeric forms of α-tocopherol from food, fortified food and multivitamins. The Upper Limits (ULs) apply to any forms of supplemental α-tocopherol.

The FNB found no functional criteria of vitamin E status that reflected the response to dietary intake in infants. Thus the recommended intakes of vitamin E are based on AI, which reflects a calculated mean vitamin E intake of infants fed principally with human milk. The UL was judged not determinable by the FNB because of insufficient data on adverse effects in this age group. Table 6 lists the Adequate Intake (AI) for infants ages 0 through 12 months.

TABLE 6

Infant Adequate Intake for Vitamin E

| Infants (ages) | AI (α-tocopherol) |
|---|---|
| 0–6 months | 4.0 mg/day (~0.6 mg/kg) |
| 7–12 months | 5.0 mg/day (~0.6 mg/kg) |

Table 7 lists the Estimated Average Requirements (ERAs), Recommended Dietary Allowances (RDAs), and Upper Limits (ULs) for vitamin E for pregnant and lactating women.

TABLE 7

Recommended Vitamin E intakes

| Life Stage (ages) | EAR (α-tocopherol)$^a$ | RDA (α-tocopherol)$^a$ | UL (α-tocopherol)$^b$ |
|---|---|---|---|
| Pregnancy | 12 mg/day | 15 mg/day | 800 mg/day* 1000 mg/day** |
| Lactation | 16 mg/day | 19 mg/day | 800 mg/day* 1000 mg/day** |

$^a$includes only naturally occurring form (RRR-) and the other three synthetic 2R-stereoisomer forms (RSR-, RRS-, and RSS-) of α-tocopherol
$^b$includes any forms of supplemental α-tocopherol
*14–18 years
*>19 years Tocopherol Content of Oils and Fats Most vegetable oils are among the richest sources of tocopherols. For many oils, α-tocopherol is the major contributor to the total vitamin E activity; however, notable exceptions are soybean oil and corn oil, which have relatively high concentrations of γ-tocopherol. Most oils have either low concentrations of tocotrienols or non-at all. An exception is palm oil, which has about 14 mg α-tocotrienol, 28 mg γ-tocotrienol, and nearly 7 mg δ-tocotrienol per 100 gm oil. Among the oils, coconut oil has the lowest vitamin E activity at 0.7 mg α-TE, and wheat germ oil has the highest at 173 mg of TE per 100 g oil. Wheat germ oil also has the highest β-tocopherol content at 71 mg per 100 g. Fish liver oils have relatively high α-tocopherol concentrations. Fish body oils, like herring and menhaden oils, have moderate amounts of α-tocopherol. Much of this may be lost when fish oils are processed to make them suitable for use in foods. During hydrogenation, little or no vitamin E was lost. Shortenings, margarines, salad dressings, fried foods, baked products and nutritionals tend to reflect the tocopherol pattern of the ingredient oil. Table 8 lists the tocopherol content of several oils.

TABLE 8

Tocopherol content of oils** (per 100 g)

| | Tocopherols | | | | Tocotrienols | |
|---|---|---|---|---|---|---|
| Product | α (mg) | β (mg) | γ (mg) | δ (mg) | α (mg) | β (mg) |
| Oils - Vegetable | | | | | | |
| Canola | 21.0 | 0.1 | 4.2 | 0.04 | 0.04 | — |
| Coconut | 0.5 | — | — | 0.6 | 0.5 | 0.1 |
| Corn | 11.2 | 5.0 | 60.2 | 1.8 | — | — |
| Cottonseed | 38.9 | — | 38.7 | — | — | — |
| Olive | 11.9 | — | 0.7 | — | — | — |
| Palm | 25.6 | — | 31.6 | 7.0 | 14.6 | 3.2 |
| Palm Kernel | 6.2 | — | — | — | — | — |
| Peanut | 13.0 | — | 21.4 | 2.1 | — | — |
| Safflower | 34.2 | — | 7.1 | — | — | — |
| Sesame | 13.6 | — | 29.0 | — | — | — |
| Soybean | 7.5 | 1.5 | 79.7 | 26.6 | 0.2 | 0.1 |
| Sunflower | 48.7 | — | 5.1 | 0.8 | — | — |
| Walnut | 56.3 | — | 59.5 | 45.0 | — | — |
| Wheat germ | 133.0 | 71.0 | 26.0 | 27.1 | 2.6 | 18.1 |
| Oils - Marine | | | | | | |
| Cod liver | 22.0 | — | — | — | — | — |
| Herring | 9.2 | — | — | — | — | — |
| Menhaden | 7.5 | — | — | — | — | — |

**Table from Vitamin E in Health and Disease, edited by Lester Packer and Jurgen Fuchs; Marcel Dekker, Inc, New York, New York, 1993, p.23
Dashes denote no value or trace Vitamin E Activity The eight known tocopherols have different biological activities. The naturally occurring RRR-tocopherol has been assigned an activity of 1 mg α-TE per milligram. The relative activities of other tocopherols are listed in Table 9. The vitamin E activity of a food may be calculated by taking the sum of the values obtained by multiplying the number of milligrams of each component tocopherol by the appropriate factor given in Table 9.

TABLE 9

Vitamin E Activity of the Tocopherols and Tocotrienols**

| Tocopherol | Activity as α-TE* (mg/mg compound) |
|---|---|
| RRR-α-tocopherol | 1.0 |
| RRR-β-tocopherol | 0.5 |
| RRR-γ-tocopherol | 0.1 |
| RRR-δ-tocopherol | 0.03 |
| RRR-α-tocotrienol | 0.3 |
| RRR-β-tocotrienol | 0.05 |
| RRR-γ-tocotrienol | — |
| RRR-δ-tocotrienol | — |
| Synthetic α-tocopheryl acetate | 0.74 |

*α-tocopherol equivalents(TE)
**Table from Vitamin E in Health and Disease, edited by Lester Packer and Jurgen Fuchs; Marcel Dekker, Inc, New York, New York, 1993, p.21
Dashes denote unknown activities Gamma- to Alpha-Tocopherol Ratio The instant invention relates to a method of improving the antioxidant status of an infant by administering the required amount of vitamin E to said infant in a γ- to α-tocopherol ratio from about 1:2 γ- to α-tocopherol to about 10:1 γ- to α-tocopherol, preferably from about 1.0:1.6 γ- to α-tocopherol to about 6:1 γ- to α-tocopherol, more preferable from about 1.0:1.4 γ- to α-tocopherol to about 2:1 γ- to α-tocopherol. In certain embodiments, the vitamin E is administered in a γ- to α-tocopherol ratio from about 1:2 γ- to α-tocopherol to about 6:1 γ- to α-tocopherol.

The γ- and α-tocopherol sources may be isolated γ- and α-tocopherol components and/or oils rich in γ- and/or α-tocopherol. Acceptable oils rich in γ- and/or α-tocopherol include, for example, canola oil, safflower oil, corn oil, sunflower oil, cod liver oil, cottonseed oil, palm oil, peanut oil, sesame oil, soybean oil, walnut oil, wheat germ oil, olive oil, Herring oil, Menhaden oil and mixtures thereof.

Numerous commercial sources for the oils listed above are readily available and known to one practicing the art. For example, soybean oil, peanut oil and canola oil are available from Archer Daniels Midland of Decatur, Ill. Corn, and palm oils are available from Premier Edible Oils Corporation of Portland, Organ. Cottonseed oil and sunflower oil are available from Cargil of Minneapolis, Minn. Sesame oil and wheat germ oil are available from Vitamins Inc of Chicago, Ill. Walnut oil and safflower oil are available from California Oils Corporation of Richmond, Calif.

Based on the known tocopherol content of different oils, one skilled in the art would be able to select a fat source to achieve the desired γ- to α-tocopherol ratio of the instant invention. For example, a fat system of 100% soybean oil would typically provide a γ- to α-tocopherol ratio of about 10.6:1; a fat system of 100% corn oil would typically provide a γ- to α-tocopherol ratio of about 5.4:1; and a fat system of 100% cottonseed oil would typically provide a γ- to α-tocopherol ratio of about 0.99:1. Likewise, numerous combinations of the oils listed in Table 8 may be utilized to achieve the desired γ- to α-tocopherol ratio. For example, a 50% soybean and 50% safflower oil blend would provide a γ- to α-tocopherol ratio of about 2:1.

Alternatively, isolated γ- and/or α-tocopherol components may be admixed with oil rich in γ- and/or α-tocopherol. Based on the known tocopherol content of different oils, one skilled in the art would be able to select a fat source or blend of fats which when supplemented with γ- and/or α-tocopherol will achieve the desired γ- to α-tocopherol ratio of the instant invention. For example, α-tocopherol is blended with a fat system rich in γ-tocopherol. The fat system may be a blend of oils such as 30% of the fat system as soybean oil, 30% of the fat system as coconut oil and 40% of the fat system as high oleic safflower oil. The soy oil, coconut oil and high oleic safflower oil blend provides the required amount of γ-tocopherol to which 91 mg of RRR-α-tocopherol acetate per 1 kg of fat system is added to achieve an γ- to α-tocopherol ratio of 1.07:1.

Commercial sources for isolated γ- and α-tocopherol are readily available and known to one practicing the art. For example, RRR-α-tocopherol and RRR-α-tocopherol acetate are available from Eastman Chemical Corp. of Kingsport, Tenn.

The natural tocopherol ratio described above may be delivered in any acceptable oral dosage form. One knowledgeable in the art would be able to select an appropriate carrier to aid in the ease of administration and to improve the organoleptic properties depending on the target population, i.e. adult women or infant. The γ- to α-tocopherol ratio of the present invention may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24-hour period.

An infant may receive the required amount of natural tocopherol ratio, for example, as concentrated liquid or infant nutritional.

Infant Dietary Supplement

The γ- to α-tocopherol ratio of the instant invention may be delivered to an infant in the form of a concentrated liquid, reconstitutable particles and microparticles for example. Syrups, honeys and elixirs may be admixed with the natural tocopherol ratio to improve the flavor. Oil in water emulsions may be better suitable for oral use in infants because these are water-miscible and thus their oiliness is masked. Emulsions are well known in the pharmaceutical sciences. The supplement of this invention can be manufactured using techniques well known to those skilled in the art. Generally speaking, an emulsifying agent is dissolved in the oil. The emulsifier/oil mixture may be added directly to the water to form an oil in water emulsion. Alternatively, the emulsifying agent is dissolved in the water and the oil is added, with agitation, to the emulsifier/aqueous solution. Examples, of typical natural emulsifying agents include gelatin, egg yolk, casein, wool fat, cholesterol, acacia, tragacanth, chondrus and pectin. The mixtures require physical manipulation to achieve the emulsified physical state. Emulsification equipment includes a wide variety of agitators, homogenizers, colloid mills and ultrasonic devices.

The γ- and α-tocopherol emulsion of the instant invention may be stored in conventional containers and are dispensed in small but precise quantities or unit dosages. Such dosages are characteristically dispensed using a pipette and compressible, resilient bulb dropper assembly.

As discussed above, the FNB recommends a dose of 0.6 mg/kg of infant body weight per day for vitamin E dosage. Typically the amount of liquid required to provide a unit dose of the γ- and α-tocopherol emulsion will typically range from about 0.1 ml to about 8 ml, more preferably from about 0.5 ml to about 5.0 ml, most preferably from about 0.5 ml to about 2.0 ml.

The infant dietary supplement of the present inventive subject matter may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period.

Typically, a unit dose of the infant dietary supplement of the invention comprises at least 50% of the AI for vitamin E for infants in the γ- and α-tocopherol of the invention in 1 ml. Typically, a unit dose is administered to the infant at least once a day.

Additional nutrients may be added to the γ-/α-tocopherol dietary supplement. Optional nutrients may include a blend of antioxidants such as trans beta-carotene, cis beta-carotenes, cis alpha-carotenes, trans lycopene, cis lycopene, trans gamma-carotene, cis gamma-carotene, zeta-carotene, phytofluene, phytoene, vitamin C, cis lutein, trans lutein, cis lutein esters, trans lutein esters, cis zeaxanthin, trans zeaxanthin, cis zeaxanthin ester, trans zeaxanthin ester, beta crytoxantyhin and glutamine and other nutrients such as vitamin A, vitamin $B_1$, vitamin $B_2$, vitamin $B_6$, vitamin $B_{12}$, vitamin C, vitamin D, vitamin K, biotin, folic acid, pantothenic acid, niacin, m-inositol, calcium, phosphorus, magnesium, zinc, manganese, copper, sodium, potassium, chloride, iron, chromium, molybdenum, and selenium.

An optional infant dietary supplement of the instant invention typically supplies about 80% of the AI for vitamin E for infants in the γ- and α-tocopherol ratio of the invention per day, from about 65 to 145 mcg/day beta-cryptoxanthan, from about 100 to about 145 mcg/day lycopene, from about 40 to about 80 mcg/day alpha-carotene, from about 175 to about 355 mcg/day beta-carotene and from about 175 to about 355 mcg/day lutein/zeaxanthin. Typically, 1 ml is a unit dose which is administered to the infant at least once a day.

Alternatively, the γ-/α-tocopherol blend of the instant invention may be added to an infant nutritional.

Infant Nutritional Formula

Infant formulas are known in the art and one knowledgeable in the art would be able to adjust the formula to include the γ- to α-tocopherol ratio of the instant invention. For example, an infant formula typically contains a protein component comprising from about 6 to about 25% of the total caloric content of said infant formula; a carbohydrate component comprising from about 35 to about 50% of the total caloric content of said infant formula; and a lipid component comprising from about 30 to about 50% of the total caloric content of said infant formula. These ranges are provided as examples only, and are not intended to be limiting.

The fat component of an infant formula is an ideal source of energy for infants, not only because of its high caloric density but also because of its low osmotic activity in solution. The fat component also solubilizes fat-soluble vitamins and emulsifiers in the aqueous solution.

Based on the known tocopherol content of different oils, one skilled in the art would be able to select a fat source or blend of fats to achieve the desired γ- to α-tocopherol ratio of the instant invention as well as meet the desired fatty acid profile for the specific application. Examples of suitable fat sources typically include high oleic safflower oil, soy oil, fractionated coconut oil (medium chain triglycerides, MCT oil), high oleic sunflower oil, corn oil, canola oil, coconut, palm and palm kernel oils, marine oil, cottonseed oil, walnut, wheat germ, sesame, cod liver, peanut and specific fatty acids such as docosahexaenoic acid and arachidonic acid. Any single fat listed above, or any combination thereof, as appropriate may be utilized. Other suitable fats will be readily apparent to those skilled in the art.

Alternatively, isolated γ- and α-tocopherol may be individually added to a fat system to achieve the desired γ- to α-tocopherol ratio.

More typically, α-tocopherol is blended with a fat system rich in γ-tocopherol. A preferred fat blend typically comprises 286 mg of RRR-α-tocopherol acetate added to 1 kg of fat system. A more preferred source of lipid is an admixture of high oleic safflower oil, soy oil, and coconut oil. Especially preferred lipids include a blend of vegetable oils containing about 38-50 weight % high oleic safflower oil (HOSO), about 26-40 weight % soy oil (SO) and about 22-36 weight % coconut oil (CO). The soy oil, coconut oil and high oleic safflower oil blend typically provides the required amount of γ-tocopherol.

One knowledgeable in the art would understand that appropriate additional amounts of vitamin E may need to be provided to nutritional compositions to compensate for some loss during processing and storage of such compositions. Practitioners would also understand that the degree of unsaturation of the component oils must be considered when calculating the required amount of vitamin E. A predictable amount of the Vitamin E would be required to prevent oxidation of the component oils in the nutritional product.

Numerous commercial sources for the fats listed above are readily available and known to one practicing the art. For example, soy and canola oils are available from Archer Daniels Midland of Decatur, Ill. Corn, coconut, palm and palm kernel oils are available from Premier Edible Oils Corporation of Portland, Oreg. Fractionated coconut oil is available from Henkel Corporation of LaGrange, Ill. High oleic safflower and high oleic sunflower oils are available from SVO Specialty Products of Eastlake, Ohio. Marine oil is available from Mochida International of Tokyo, Japan. Sunflower and cottonseed oils are available from Cargil of Minneapolis, Minn. Safflower oil is available from California Oils Corporation of Richmond, Calif. DHA is available from Martek Biosciences Corporation of Columbia, Md. Arachidonic acid is available from Genzyme Corporation of Cambridge, Mass.

Additional components of the infant formula typically include, for example, protein, carbohydrates, vitamins and minerals. Protein is needed for growth, synthesis of enzymes and hormones, and replacement of protein lost from the skin and in urine and feces. These metabolic processes determine the need for both the total amount of protein in a feeding and the relative amounts of specific amino acids. The adequacy of the amount and type of protein in a feeding for infants is determined by measuring growth, nitrogen absorption and retention, plasma amino acids, certain blood analytes and metabolic responses.

The proteins that may be utilized in the infant nutritional products of the invention include any proteins or nitrogen source suitable for human consumption. Such proteins are well known by those skilled in the art and can be readily selected when preparing such products. Examples of suitable protein sources for an infant typically include casein, whey, condensed skim milk, nonfat milk, soy, pea, rice, corn, hydrolyzed protein, free amino acids, protein sources which contain calcium in a colloidal suspension with the protein. Any single protein listed above, or any combination thereof, as appropriate may be utilized. Other suitable proteins will be readily apparent to those skilled in the art.

A preferred protein system typically comprises 7% whey protein concentrate and 93% nonfat milk.

Commercial protein sources are readily available and known to one practicing the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa. Additionally, mineral enriched proteins are available from New Zealand Milk Products of Santa Rosa, Calif. and Protein Technologies International of Saint Louis, Mo.

The third component of the infant formula of this invention is a source of carbohydrates. Carbohydrate is a major source of readily available energy that the infant needs for growth and that protects the infant from tissue catabolism. In human milk and most standard milk-based infant formulas, the carbohydrate is lactose.

The carbohydrates that may be used in the infant formula can vary widely. Examples of carbohydrates suitable for infants typically include hydrolyzed cornstarch, maltodextrin, glucose polymers, sucrose, lactose, corn syrup, corn syrup solids, rice syrup, glucose, fructose, high fructose corn syrup and indigestible oligosaccharides such as fructooligosaccharides (FOS). Any single carbohydrate listed above, or any combination thereof, as appropriate may be utilized. Other suitable carbohydrates will be readily apparent to those skilled in the art.

Typically, lactose is the preferred carbohydrate source that comprises 100% of the carbohydrate component.

Commercial sources for the carbohydrates listed above are readily available and known to one practicing the art. For example, corn syrup solids are available from Cerestar USA, Inc in Hammond, Ind. Glucose and rice based syrups are available from California Natural Products in Lathrop, Calif. Various corn syrups and high fructose corn syrups are available from Cargil in Minneapolis, Minn. Fructose is available from A.E. Staley in Decatur, Ill. Maltodextrin, glucose polymers, hydrolyzed corn starch are available from American Maize Products in Hammond, Ind. Sucrose is available from Domino Sugar Corp. in New York, N.Y. Lactose is available from Foremost in Baraboo, Wis. and indigestible oligosaccharides such as FOS are available from Golden Technologies Company of Golden, Colo.

The infant formula of the present invention typically includes supplemented vitamins and minerals.

Infants require the electrolytes sodium, potassium and chloride for growth and for acid-base balance. Sufficient intakes of these electrolytes are also needed for replacement of losses in the urine and stool and from the skin. Calcium, phosphorus and magnesium are needed for proper bone mineralization. For bones to grow, adequate amounts of these minerals must be present in a feeding. Infants may develop rickets or osteopenia if they do not receive adequate amount of calcium and phosphorus in their diet. Phosphorus and magnesium are also found in intracellular fluid. These minerals are needed for the growth and function of soft tissue.

Trace minerals are associated with cell division, immune function and growth. Consequently, provision of sufficient amounts of trace minerals is needed for rapid growth in infants. Another trace mineral, iron, is important for the synthesis of hemoglobin, myoglobin and iron-containing enzymes. However, it is not certain that infants need the recommended amounts of iron during the first 2 months of life. Also, it is estimated that infants have sufficient iron stores without receiving iron supplementation, if blood loss is small, until 2 months of age. Consequently, the infant formula of the instant invention may be optionally fortified with iron. Zinc is needed for growth, for the activity of numerous enzymes, and for DNA, RNA and protein synthesis. Copper is necessary for the activity of several important enzymes. Manganese is needed for the development of bone and cartilage and is important in the synthesis of polysaccharides and glyoproteins.

Vitamin A is a fat-soluble vitamin essential for normal bone formation and for maintenance of specialized epithelial surfaces, which include mucous membranes of the eyes; the mucosa of the respiratory, gastrointestinal and genitourinary tracts; the ducts of various glands; and the skin, hair, gums and teeth. Vitamin D is important for absorption of calcium and to a lesser extent, phosphorus, and for the development of bone. Vitamin K is important in the biosynthesis of prothrombin and other blood-clotting factors. Newborn infants have little reserve of vitamin K and do not have a source for vitamin K until after intestinal bacteria are established, thereby becoming an important source of vitamin K for the infant. Vitamin E (tocopherol) prevents peroxidation of polyunsaturated fatty acids in the cell, thus preventing tissue damage. Infants may develop hemolytic anemia and vitamin E deficiency when fed feedings low in vitamin E and high in iron and polyunsaturated fatty acids.

Vitamin C is necessary in the formulation of collagen and dentine and is required for the metabolic reactions of amino acids and for the synthesis of anti-inflammatory steroids by the adrenal glands. Folic acid is important in amino acid and nucleotide metabolism. Serum folate concentrations have been shown to fall below normal after 2 weeks of age in infants with low folic acid intakes. Thiamine (vitamin B1) functions as a coenzyme in oxidative metabolism. Roboflavin (vitamin B2) assists in the transfer of oxygen from plasma to substrate of tissue cells and also functions in hydrogen transport mechanisms. Niacin plays an essential role in the electron transport involved in cellular respiration and appears to be involved in pigment and fat metabolism. Pyridoxine (vitamin B6) functions as a coenzyme in amino acid decarboxylation, in transamination, and in tryptophan metabolism. Vitamin B12 is essential in the formulation of DNA, nuclear maturation, and cell division. Pantothenic acid functions as an important cofactor for all acylation reaction in the body. It is involved in gluconeogenesis, synthesis of fatty acids, and sterols, and cellular metabolism of fats, carbohydrates, and proteins.

Based on the requirements described above, the infant formula requires fortification to insure that a developing infant receives adequate amounts of vitamins and minerals while not over fortifying and possibly causing, for example, hypercalcemia. Using the recommendations of the FNB, one skilled in the art can readily calculate how much of a vitamin or mineral source should be added to the nutritional product in order to deliver the desired amount of a vitamin or mineral. Practitioners also understand that appropriate additional amounts of vitamin and mineral ingredients need to be provided to nutritional compositions to compensate for some loss during processing and storage of such compositions.

Examples of vitamins and minerals that may be added to the infant formula of the instant invention typically include vitamin A, vitamin $B_1$, vitamin $B_2$, vitamin $B_6$, vitamin $B_{12}$, vitamin C, vitamin D, vitamin K, vitamin E, biotin, folic acid, pantothenic acid, niacin, m-inositol, calcium, phosphorus, magnesium, zinc, manganese, copper, sodium, potassium, chloride, iron and selenium. The additional nutrients chromium, molybdenum, iodine, taurine, carnitine and choline may also require supplementation. As discussed above, the infant formula will include the natural form of vitamin E in the $\gamma$- to $\alpha$-tocopherol ratio of the instant invention.

Typically, 100% of the AI for vitamin E in the $\gamma$- to $\alpha$-tocopherol ratio of the instant invention is added to a liter of infant formula, which is a typical volume of formula consumed by an infant in a day.

The infant formula of this invention can be manufactured using techniques well known to those skilled in the art. While manufacturing variations are certainly well known to those skilled in the nutritional formulation arts, a few of the manufacturing techniques are described in detail in the Examples. Generally speaking a protein-in-oil blend is prepared containing all oils, any emulsifier, the fat-soluble vitamins and a portion of the protein. A second slurry is prepared by mixing the carbohydrate and minerals together. The protein-in-oil and any remaining protein are added to the carbohydrate/ mineral slurry. The resulting mixture is homogenized, heat processed, standardized with water-soluble vitamins. The concentrated formula may be filed into appropriate packaging and sterilized; aseptically filed into sterile packaging; or dried and filed into appropriate packaging. The resulting powder may be milled to a specific particle size and/or agglomerized to modify particle size and mixability characteristics. Those skilled in the nutritional formulation arts would also be able to dry blend the individual starting materials and add the liquid ingredients through agglomeration or during the dry blending step. The concentrated blend may also be diluted and filed into appropriate packaging and sterilized or aseptically filed into sterile packaging.

Numerous types of packaging are readily available and known to one practicing the art. Desirable packaging characteristics include: effective protection against impact, light, and heat; ease of opening; and efficient sealing for storage stability.

Human Milk Fortifier

Premature infants require additional nutrients to support their growth and are at risk for the diseases related to prematurity related to oxidation. Therefore, a human milk fortifier would be a preferred method to deliver the γ- to α-tocopherol ratio of the instant invention. A human milk fortifier of this invention is a powder which when added to human milk delivers the preferred γ- to α-tocopherol ratio and supplements the levels of protein, fat, vitamins and minerals.

Although not intended to limit the invention in any manner, but to merely serve as a general guideline, the human milk fortifier powder of this invention will typically provide the following macronutrient distribution. The protein component will typically be present in an amount of from about 24 wt/wt % to about 55 wt/wt % of the fortifier powder. The fat component will typically be present in an amount of from about 1 wt/wt % to about 30 wt/wt % of the fortifier powder. The carbohydrate component will typically be present in an amount of from about 15 wt/wt % to about 75 wt/wt % of the fortifier powder. Additionally, the amount of powder required to provide a unit dose of the fortifier will typically range from about 0.5 gm to about 10 gm of powder in a unit dose. The caloric density is typically from about 1.0 kcal/gm powder to about 8.5 kcal/gm powder.

The first component of the fortifier powder of this invention is a source of protein. As in the term infant, the preterm infant requires protein for growth, synthesis of enzymes and hormones, and replacement of protein lost from the skin and in urine and feces. These metabolic processes determine the need for both the total amount of protein in a feeding and the relative amounts of specific amino acids. The adequacy of the amount and type of protein in a feeding for infants is determined by measuring growth, nitrogen absorption and retention, plasma amino acids, certain blood analytes and metabolic responses.

As stated above, the protein component will typically be present in an amount of from about 24 wt/wt % to about 55 wt/wt % of the fortifier powder. The proteins that may be utilized in the nutritional products of the invention include any proteins or nitrogen source suitable for human consumption. Such proteins are well known by those skilled in the art and can be readily selected when preparing such products. Examples of suitable protein sources for a premature infant typically include casein, whey, condensed skim milk, nonfat milk, soy, pea, rice, corn, hydrolyzed protein, free amino acids, protein sources which contain calcium in a colloidal suspension with the protein. Any single protein listed above, or any combination thereof, as appropriate may be utilized. Other suitable proteins will be readily apparent to those skilled in the art.

The preferred protein system will typically be comprised of about 51 wt/wt % of the protein component as whey protein concentrate and about 49 wt/wt % of the protein component as nonfat dry milk, which corresponds to about 60 wt/wt % of the protein component as whey and about 40 wt/wt % of the protein component as casein.

Commercial protein sources are readily available and known to one practicing the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa. Additionally, mineral enriched proteins are available from New Zealand Milk Products of Santa Rosa, Calif. and Protein Technologies International of Saint Louis, Mo.

The second component of the fortifier powder of this invention is a source of fat. Fat is an ideal source of energy for LBW infants, not only because of its high caloric density but also because of its low osmotic activity in solution.

As stated above, the fat component will typically be present in an amount of from about 1 wt/wt % to about 30 wt/wt % of the fortifier powder. Examples of suitable fat sources typically include high oleic safflower oil, soy oil, fractionated coconut oil (medium chain triglycerides, MCT oil), high oleic sunflower oil, corn oil, canola oil, coconut, palm and palm kernel oils, marine oil, cottonseed oil and specific fatty acids such as docosahexaenoic acid and arachidonic acid. Any single fat listed above, or any combination thereof, as appropriate may be utilized. Other suitable fats will be readily apparent to those skilled in the art Docosahexaenoic acid (DHA) is an omega-3 fatty acid and is thought to be essential for the proper brain and vision development of infants because it is the most abundant long chain polyunsaturated fatty acid (PUFA) in the brain and retina. Although a metabolic pathway exists in mammals for the biosynthesis of DHA from dietary linolenic acid, this pathway is bioenergetically unfavorable and mammals are thought to obtain most of their DHA from dietary sources. In the case of infants, the most likely source would be human milk. Indeed, DHA is the most abundant 20 carbon omega-3 PUFA in human milk. However, human milk DHA content will vary greatly depending on the diet of the mother. If the mother eats fish high in DHA often, her milk will contain higher DHA levels, while a mom with less access to fish will have lower DHA levels in her milk. Consequently, human milk may require DHA supplementation to insure that the preterm infant is receiving sufficient amounts of DHA. Preferably, DHA supplementation is accompanied by arachidonic acid supplementation. U.S. Pat. No. 5,492,938 to Kyle et al. describes a method of obtaining DHA from dinoflagellates and its use in pharmaceutical composition and dietary supplements.

Typically, MCT oil is the preferred fat source, which comprises 100% of the fat component. This fat source, at this level provides well-tolerated fat calories to the premature infant in addition to providing a vehicle for the desired γ- to α-tocopherol ratio of the invention, other fat-soluble vitamins and emulsifiers. Since MCT oil (fractionated coconut oil) contains negligible levels of γ- and α-tocopherol, the human milk fortifier is fortified with isolated γ- and α-tocopherol to achieve the γ- to α-tocopherol ratio of the instant invention.

Numerous commercial sources for the fats listed above are readily available and known to one practicing the art. For example, soy and canola oils are available from Archer Daniels Midland of Decatur, Ill. Corn, coconut, palm and palm kernel oils are available from Premier Edible Oils Corporation of Portland, Oreg. Fractionated coconut oil is available from Henkel Corporation of LaGrange, Ill. High oleic safflower and high oleic sunflower oils are available from SVO Specialty Products of Eastlake, Ohio. Marine oil is available from Mochida International of Tokyo, Japan. Sunflower and cottonseed oils are available from Cargil of Minneapolis, Minn. Safflower oil is available from California Oils Corporation of Richmond, Calif. DHA is available from Martek Biosciences Corporation of Columbia, Md. Arachidonic acid is available from Genzyme Corporation of Cambridge, Mass.

An emulsifier is typically incorporated into the fortifier powder. Emulsifiers help the water soluble and insoluble components of the fortifier powder incorporate into the human milk. Examples of suitable emulsifiers typically include soya bean lecithin, polyoxythylene stearate, polyoxyethylene sorbitan mono-oleate, polyoxyethylene sorbitan monopalmitate, polyoxyethylene sorbitan monostearate, ammonium phosphatides, polyoxyethylene sorbitan monolaurate, citric acid esters of mono and diglycerides of fatty acids, tartaric acid esters of mono and diglycerides of fatty acids.

The preferred emulsifier source is natural soy lecithin. The amount of emulsifier will typically be present in an amount of from about 1 wt/wt % to about 10 wt/wt % of the fat component, which corresponds to about 0.1 wt/wt % to about 1 wt/wt % of the fortifier powder.

Numerous commercial sources for the emulsifiers listed above are readily available and known to one practicing the art. For example, soya bean lecithin is available from Archer Daniels Midland Company in Decatur, Ill. Polyoxythylene stearate, polyoxyethylene sorbitan mono-oleate, polyoxyethylene sorbitan monopalmitate, polyoxyethylene sorbitan monostearate, polyoxyethylene sorbitan monolaurate, citric acid esters of mono and diglycerides of fatty acids, and tartaric acid esters of mono and diglycerides of fatty acids are available from Quest in Owings Mills, Md.

The third component of the fortifier powder of this invention is a source of carbohydrates. Carbohydrate is a major source of readily available energy that the LBW infant needs for growth and that protects the infant from tissue catabolism. In human milk and most standard milk-based infant formulas, the carbohydrate is lactose. LBW infants may be unable to fully digest lactose because lactase activity in the fetal intestine is not fully developed until late in gestation (36 to 40 weeks). On the other hand, sucrase activity is maximal by 32 weeks' gestation, and glucosoamylase activity, which digests corn syrup solids (glucose polymers), increase twice as rapidly as lactase activity during the third trimester.

As noted above, the carbohydrates will typically be present in an amount of from about 15 wt/wt % to about 75 wt/wt % of the fortifier powder. The preferred carbohydrate level and source is selected to decrease osmolality and viscosity of the reconstituted product. The preferred carbohydrate source is 100% of the carbohydrate component as corn syrup.

The carbohydrates that may be used in the fortifier powder can vary widely. Examples of carbohydrates suitable for preterm infants typically include hydrolyzed cornstarch, maltodextrin, glucose polymers, sucrose, corn syrup, corn syrup solids, rice syrup, glucose, fructose, lactose, high fructose corn syrup and indigestible oligosaccharides such as fructooligosaccharides (FOS). Any single carbohydrate listed above, or any combination thereof, as appropriate may be utilized.

Commercial sources for the carbohydrates listed above are readily available and known to one practicing the art. For example, corn syrup solids are available from Cerestar USA, Inc in Hammond, Ind. Glucose and rice based syrups are available from California Natural Products in Lathrop, Calif. Various corn syrups and high fructose corn syrups are available from Cargil in Minneapolis, Minn. Fructose is available from A.E. Staley in Decatur, Ill. Maltodextrin, glucose polymers, hydrolyzed corn starch are available from American Maize Products in Hammond, Ind. Sucrose is available from Domino Sugar Corp. in New York, N.Y. Lactose is available from Foremost in Baraboo, Wis. and indigestible oligosaccharides such as FOS are available from Golden Technologies Company of Golden, Colo.

The osmolality of the fortified human milk plays an important role in the infant's tolerance of their feedings such as abdominal distention and vomiting/spit-up. Osmolality of the fortified human milk is tied to the level and source of carbohydrate utilized in the fortifier powder. The osmolality of the fortifier powder of the instant invention reconstituted in human milk is typically less than about 400 mOsm/kg water. The substitution of fat for some of the carbohydrate in the fortifier powder of the instant invention serves to reduce the osmolality of fortified human milk by replacing the carbohydrate, which has a high osmotic activity with fat, which has a low osmotic activity. The type of carbohydrate incorporated into the fortifier powder also impacts the osmolality of the fortified human milk. The more hydrolyzed the carbohydrate source (higher DE) the higher the osmotic activity. Additionally, partially hydrolyzed carbohydrate sources may further increase the osmolality when reconstituted with human milk due to further hydrolysis by human milk amylase. Based on the DE values for carbohydrates, one skilled in the art can readily select the carbohydrate source or combination of carbohydrates that will result in the preferred osmolality of the reconstituted fortifier powder/human milk solution.

As stated above, viscosity is also a characteristic of carbohydrates. Viscosity of the reconstituted fortifier powder/human milk solution plays a role in suspending the insoluble minerals during feeding. While higher viscosities tend to reduce insoluble mineral fallout, the higher viscosity can cause tube/nipple clogging. A clogged feeding tube in a continuous feeding apparatus requires additional attention by the nursing staff who will have to unclog the tube, reset the pump system, which may require a new preparation of fortified human milk. More importantly, a clogged tube prevents the timely delivery of much needed nutrients to a premature infant. The viscosity of the reconstituted fortifier powder/human milk solution of the instant invention is typically less than about 30 cps. Viscosity is inversely related to osmolality. The more hydrolyzed a starch is (higher DE), the lower the viscosity and the higher the osmolality. Based on the DE values for carbohydrates, one skilled in the art can readily select the carbohydrate source or combination of carbohydrates that will drive the viscosity and osmolality characteristics of the reconstituted fortifier powder/human milk solution to the preferred levels.

The fourth component of the fortifier powder of the present invention typically includes supplemented vitamins and minerals.

The preterm infant requires the electrolytes sodium, potassium and chloride for growth and for acid-base balance. Sufficient intakes of these electrolytes are also needed for replacement of losses in the urine and stool and from the skin. Calcium, phosphorus and magnesium are needed for proper bone mineralization. For bones to grow, adequate amounts of these minerals must be present in a feeding. LBW infants may develop rickets or osteopenia if they do not receive adequate amount of calcium and phosphorus in their diet. Phosphorus and magnesium are also found in intracellular fluid. These minerals are needed for the growth and function of soft tissue. Human milk does not provide enough calcium or phosphorus, even if these minerals were to be totally absorbed and retained, which they are not.

Trace minerals are associated with cell division, immune function and growth. Consequently, provision of sufficient amounts of trace minerals is needed for rapid growth in LBW infants. Human milk does not provide sufficient amounts of the trace minerals, especially zinc and copper, to meet the needs of a growing LBW infant. Another trace mineral, iron, is important for the synthesis of hemoglobin, myoglobin and iron-containing enzymes. However, it is not certain that LBW infants need the recommended amounts of iron during the first 2 months of life. The anemia of prematurity occurring shortly after birth cannot be avoided by giving supplemental iron. Also, the preterm infant is estimated to have sufficient iron stores without receiving iron supplementation, if blood loss is small, until 2 months of age. Consequently, the powdered human milk fortifier of the instant invention is low in iron. Zinc is needed for growth, for the activity of numerous enzymes, and for DNA, RNA and protein synthesis. Copper is necessary for the activity of several important enzymes. It is estimated that about 75% of the copper in a term neonate is accumulated during the last 10 to 12 weeks in utero. Consequently, LBW infants, especially those born weighing less than 1500 gm, are likely to have low copper stores. Manganese is needed for the development of bone and cartilage and is important in the synthesis of polysaccharides and glyoproteins.

LBW infants are likely to need more of most vitamins than provided by human milk alone because of low vitamin stores at birth, low intake of feedings, poor absorption of vitamins and clinical conditions requiring increased vitamin intakes.

Vitamin A is a fat-soluble vitamin essential for growth, cell differentiation, vision and the immune system. The vitamin A stores in LBW infants are adequate shortly after birth but decrease soon thereafter. Therefore, preterm infants may require higher intakes of vitamin A than term infants. Vitamin D is important for absorption of calcium and to a lesser extent, phosphorus, and for the development of bone. For many years it was thought that poor bone development observed in LBW infants was due to insufficient vitamin D intake and metabolism and the LBW infants required significantly greater vitamin D intake than term infants. It is now recognized that calcium and phosphorus intakes are more important than vitamin D for bone growth in preterm infants. Vitamin E (tocopherol) prevents peroxidation of polyunsaturated fatty acids in the cell, thus preventing tissue damage. LBW infants may develop hemolytic anemia and vitamin E deficiency when fed feedings low in vitamin E and high in iron and polyunsaturated fatty acids. Additionally, preterm milk contains very low levels of vitamin K.

As are several other water-soluble vitamins, vitamin C is low in mature preterm milk. Folic acid is important in amino acid and nucleotide metabolism. Serum folate concentrations have been shown to fall below normal after 2 weeks of age in LBW infants with low folic acid intakes. Additionally, several B vitamins are present at low concentrations in preterm milk.

The variability of human milk vitamin and mineral concentrations and the increased needs of the preterm infant requires a minimal fortification to insure that a developing premature infant is receiving adequate amounts of vitamins and minerals while not over fortifying and possibly causing, for example, hypercalcemia. Using the recommendations of the FNB, one skilled in the art can readily calculate how much of a vitamin or mineral source should be added to the nutritional product in order to deliver the desired amount of a vitamin or mineral. Practitioners also understand that appropriate additional amounts of vitamin and mineral ingredients need to be provided to nutritional compositions to compensate for some loss during processing and storage of such compositions.

Examples of supplemental vitamins and minerals in the fortifier powder of the instant invention typically include vitamin A, vitamin $B_1$, vitamin $B_2$, vitamin $B_6$, vitamin $B_{12}$, vitamin C, vitamin D, vitamin E, vitamin K, biotin, folic acid, pantothenic acid, niacin, m-inositol, calcium, phosphorus, magnesium, zinc, manganese, copper, sodium, potassium, chloride, iron and selenium. The additional nutrients chromium, molybdenum, iodine, taurine, carnitine and choline may also require supplementation. As discussed above, the fortifier powder will include the natural form of vitamin E in the γ- to α-tocopherol ratio of the instant invention. Preferably, a unit dose typically comprises at least about 25% of the AI for infants for vitamin E.

The nutritional powder of this invention can be manufactured using techniques well known to those skilled in the art. While manufacturing variations are certainly well known to those skilled in the nutritional formulation arts, a few of the manufacturing techniques are described in detail in the Examples. Generally speaking an oil blend is prepared containing all oils, any emulsifier, and the fat soluble vitamins. Two more slurries (carbohydrate and protein) are prepared separately by mixing the carbohydrate and minerals together and the protein in water. The two slurries are then mixed together with the oil blend. The resulting mixture is homogenized, heat processed, standardized with water soluble vitamins, and dried. The resulting powder may be milled to a specific particle size and/or aggolmerized to modify particle size and mixability characteristics. Those skilled in the nutritional formulation arts would also be able to dry blend the individual starting materials and add the liquid ingredients through agglomeration or during the dry blending step.

Individual unit dose size packages are preferred over bulk packaging. Because of the small volumes of milk administered to premature infants over the course of a days feeding, small volumes of fortified human milk are prepared. Powder sterility in a bulk container that has been repeatedly opened, powder scooped out, recovered and stored is always a concern in a hospital environment. Individual unit doses allow for addition of small amounts of powder to human milk without the possibility of contamination of the remaining powder since all of the powder is used in a single preparation. As noted above, the unit dose of the invention typically is the amount of from about 0.5 gm to about 10 gm of fortifier powder in a unit dose. Depending on the volume of a days feeding, from about 1 to about 4 unit doses will be added to about 25 ml to about 100 ml, respectively.

Numerous types of containers are readily available and known to one practicing the art. Examples of container types typically include packets or sachets, which may be manufactured of paper, foil and plastic film, and foil and plastic film coated paper; and ampoules which may be manufactured of plastic, reinforced paper and glass.

Pregnant and Lactating Women Dietary Supplement

It is known that adults preferentially utilize natural vitamin E roughly twice that of synthetic vitamin E. Further, it is known that the human placenta delivers natural vitamin E to the fetus significantly more efficiently than synthetic vitamin E. This was shown in a study where pregnant women were given different amounts of vitamin E in a capsule that contained both the natural and synthetic forms for 5 days prior to giving birth (Acuff, et al, American Journal of Clinical Nutrition 1998; 67:459-6428). At delivery, nearly twice the concentration of the natural vitamin E was found in the mother's own blood and nearly 3.5 times the amount of natural vitamin E in their placental cord blood than the synthetic vitamin E, regardless of the amount given.

The inventors have taken advantage of this mode of delivery for vitamin E by supplementing the pregnant woman with the desired γ- to α-tocopherol ratio. The third embodiment of the invention is a method of promoting antioxidant status of an infant by administering to the pregnant woman the required amount of vitamin E in a γ- to α-tocopherol ratio from about 1:2 γ- to α-tocopherol to about 10:1 γ- to α-tocopherol, preferably from about 1.0:1.6 γ- to α-tocopherol to about 6:1 γ- to α-tocopherol, more preferable from about 1.0:1.4 γ- to α-tocopherol to about 2:1 γ- to α-tocopherol. In certain embodiments, the vitamin E is administered in a γ- to α-tocopherol ratio from about 1:2 γ- to α-tocopherol to about 6:1 γ- to α-tocopherol.

As used herein a "prenatal relevant amount" of a vitamin or mineral is an amount, in an intended daily dose of a dietary supplement which is at least 10% of the FNB RDA of the vitamin and/or mineral for a pregnant woman, preferably at least 25% of the FNB RDA, more preferably at least 50% of the FNB RDA, more preferably at least 75% of the FNB RDA, most preferably about 100% of the FNB RDA of the vitamin and/or mineral for a pregnant woman. By way of example, the FNB RDA value for vitamin E for pregnant women is 15 mg of α-tocopherol per day, 770 mcg/day of vitamin A, 27 mg/day of iron, 11 mg/day of zinc, 600 mcg/day of folate, 85 mg/day of vitamin C and 60 mcg/day of selenium. As discussed by the FNB, there was not sufficient functional data to generate an RDA for all of the nutrients, thus the recommended intakes are based on AI. For example, the FNB AI for pantothenic acid is 6 mg/day for a pregnant woman, 30 mcg/day for biotin, 5.0 mcg/day for vitamin D, and 90 mcg/day for vitamin K.

Additionally, the inventors discovered that the secretion of vitamin E into breast milk further discriminates between natural and synthetic vitamin E carried in plasma lipoproteins.

The inventors have taken advantage of this mode of delivery by supplementing the lactating woman with the desired γ-tocopherol and α-tocopherol ratio. The naturally fortified human milk can then be fed to the infant. The invention also relates to a method of promoting antioxidant status of an infant fed breast milk by administering to a lactating woman the required amount of vitamin E a γ- to α-tocopherol ratio from about 1:2 γ- to α-tocopherol to about 10:1 γ- to α-tocopherol, preferably from about 1.0:1.6 γ- to α-tocopherol to about 6:1 γ- to α-tocopherol, more preferable from about 1.0:1.4 γ- to α-tocopherol to about 2:1 γ- to α-tocopherol. In certain embodiments, the vitamin E is administered in a γ- to α-tocopherol ratio from about 1:2 γ- to α-tocopherol to about 6:1 γ- to α-tocopherol.

As used herein a "lactating relevant amount" of a vitamin or mineral is an amount, in an intended daily dose of a dietary supplement which is at least 10% of the FNB RDA of the vitamin and/or mineral for a lactating woman, preferably at least 25% of the FNB RDA, more preferably at least 50% of the FNB RDA, more preferably at least 75% of the FNB RDA, most preferably about 100% of the FNB RDA of the vitamin and/or mineral for a lactating woman. By way of example, the FNB RDA value for vitamin E for lactating women is 19 mg of α-tocopherol per day, 1,300 mcg/day of vitamin A, 9 mg/day of iron, 12 mg/day of zinc, 500 mcg/day of folate, 120 mg/day of vitamin C and 70 mcg/day of selenium. As discussed by the FNB, there was not sufficient functional data to generate an RDA for all of the nutrients, thus the recommended intakes are based on AI. For example, the FNB AI for pantothenic acid is 7 mg/day for a lactating woman, 35 mcg/day for biotin, 5.0 mcg/day for vitamin D, and 90 mcg/day for vitamin K.

Using the recommendations of the FNB (Table 7) for pregnant and lactating women, one skilled in the art can readily calculate how much total vitamin E should be added to the dietary supplement in order to deliver the desired amount of γ- to α-tocopherol ratio of this invention. Practitioners also understand that appropriate additional amounts of the vitamin E ratio need be provided to compensate for some loss during processing and storage of such compositions.

The composition of the present inventive subject matter may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period.

Optionally, the dietary supplement of the present inventive subject matter for the dosage form to combine various forms of release, which include, for example, immediate release, extended release, pulse release, variable release, controlled release, timed release; sustained release, delayed release, long acting, and combinations thereon. The ability to obtain immediate release, extended release, pulse release, variable release, controlled release, timed release, sustained release, delayed release, long acting characteristics and combinations thereof is performed using well known procedures and techniques. Each of these specific techniques or procedures for obtaining the release characteristics are well known to those of ordinary skill in the art.

Any orally acceptable dosage form, and combinations thereof, are contemplated by the inventive subject matter. Examples of such dosage forms include, for example, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, and combinations thereof. The preparation of the above dosage forms are well known to persons of ordinary skill in the art.

The following procedures represent typical methods of preparing formulations falling within the scope of the inventive subject matter. For example, quick dissolve tablets may be prepared by mixing the formulation with agents such as sugars and cellulose derivatives, which promote dissolution or disintegration of the resultant tablet after oral administration, usually within 30 seconds.

Chewable tablets, for example, may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are well versed in the processes and the machinery used as the chewable dosage form is a very common dosage form in the pharmaceutical industry.

Film coated tablets, for example, may be prepared by coating tablets using techniques such as rotating pan coating methods or air suspension methods to deposit a contiguous film layer on a tablet. This procedure is often done to improve the aesthetic appearance of tablets, but may also be done to improve the swallowing of tablets, or to mask an obnoxious odor or taste, or to improve to usual properties of an unsightly uncoated tablet.

Compressed tablets, for example, may be prepared by mixing the formulation with excipients intended to add binding qualities to disintegration qualities. The mixture is either directly compressed or granulated then compressed using methods and machinery quite well known to those in the industry. The resultant compressed tablet dosage units are then packaged according to market need, i.e., unit dose, rolls, bulk bottles, blister packs, etc.

The γ to α-tocopherol ratio of the instant invention is preferably delivered in soft gelatin capsules, more commonly known as soft gels. Soft gels are widely used in the pharmaceutical industry as an oral dosage form containing many different types of pharmaceutical and vitamin products. Soft gels are available in a great variety of sizes and shapes, including round shapes, oval shapes, oblong shapes, tube shapes and other special types of shapes such as stars. The finished capsules or soft gels can be made in a variety of colors. Also, opacifiers may be added to the shell. Soft gels are predominantly employed for enclosing liquids, more particularly oily solutions, suspensions or emulsions. Filling materials normally used are vegetable, animal or mineral oils, liquid hydrocarbons, volatile oils and polyethylene glycols.

The soft gelatin capsules containing the γ- to α-tocopherol ratio of this invention can be manufactured using techniques well known to those skilled in the art. U.S. Pat. Nos. 4,935,243, 4,817,367 and 4,744,988 are directed to the manufacturing of soft gelatin capsules. Manufacturing variations are certainly well known to those skilled in the pharmaceutical sciences. Typically, soft gels comprise an outer shell primarily made of gelatin, a plasticizer, and water, and a fill contained within the shell. The fill may be selected from any of a wide variety of substances that are compatible with the gelatin shell.

Generally speaking, a gelatin capsule manufacturing system is comprised of three main systems: a sheet forming unit, a capsule forming unit, and a capsule recovery unit. A gelatin hopper supplies the gelatin to the tank where a heater melts the gelatin. The melted gelatin is delivered to the spreading box where the desired size, shape and thickness of the gelatin sheet is formed and discharged out of the spreader box to a cooling drum. The cooling drum cools the gelatin sheet as the gelatin sheet is transported to the capsule-forming unit. A pair of cooled gelatin sheets is inserted between a pair of die rolls fitted with the desired die heads in the capsule-forming unit. At the same time, the fill liquid nozzle is positioned so as to discharge the desired amount of fill liquid between two gelatin sheets. The discharging timing is adjusted so that the recess formed by the die heads are filed with fill liquid as the gelatin sheets are brought into contact with each other, which allows filled capsules to be formed. Die roll scraping brushes remove the formed gelatin capsules from the die heads. The gelatin capsules are subsequently collected into a bulk container for storage prior to filing into the desired container.

Soft gels present a number of advantages over other forms of oral administration. They are, for instance, odorless and tasteless, easy to swallow, and their swelling properties and solubility in water ensure that the active substances are easily released in the stomach. The soft gel capsule is the preferred method of delivery for the instant invention due to vitamin E sensitivity to oxidation and light.

Typically, the dietary supplement unit dosage for the pregnant or lactating woman is one soft gel capsule comprising at least 50% of the RDA for vitamin E in the γ- to α-tocopherol ratio of the instant invention. Typically one soft gel cap is administered per day to the pregnant or lactating woman.

Optionally, additional nutrients relevant to the pregnant or lactating woman, such as vitamin C, iron, vitamin B complex, and vitamin D may be added to the vitamin E dietary supplement of the invention. Typically, at least 25% of the RDA or AI, of the supplemental nutrients discussed above, for a pregnant or lactating women is added to one dose of the vitamin E dietary supplement. Typically a single dose, such as a compressed tablet, is administered per day to the pregnant or lactating woman.

Alternatively, this invention relates to a liquid, ready to consume low pH beverages that provide at least 10% of the FNB RDA for vitamin E for pregnant or lactating women in the desired γ- to α-tocopherol ratio of this invention, at least 30% of the AI for calcium and at least 50% of the RDA for vitamin C in one serving (12 oz or 355 ml.)

Using the recommendations of the FNB (Table 7) for pregnant and lactating women, one skilled in the art can readily calculate how much total vitamin E should be added to the ready to consume low pH beverages in order to deliver the desired amount of γ- to α-tocopherol ratio of this invention. Practitioners also understand that appropriate additional amounts of the vitamin E ratio need be provided to compensate for some loss during processing and storage of such compositions.

Thus, there is disclosed a liquid beverage comprising water, calcium glycerophosphate, vitamin C, vitamin E in the γ- to α-tocopherol ratio of this invention that is supplied in the form of an emulsion which comprises vitamin E, vegetable oil and a non-hydrolyzed gum selected from gum arabic, gum tragacanth and xanthan gum and an acidulant. The vegetable oil is preferably selected from corn oil and partially hydrogenated soybean oil. The beverage has a pH of from about 2.8 to 4.6 and wherein the beverage contains from about 7.2 to 18% by wt. calcium on a dry weight basis. The beverage may also contain vitamin D that is supplied in the emulsion described above.

The acidulants used to lower the pH of the beverage can be those commonly used in the food and beverage industry to impart tart and/or sour tastes. Combinations of citric and lactic acids are preferred. More preferred is a 75% by weight lactic acid/25% acetic acid acidulant. The beverage of this invention may also contain ascorbic acid, preservatives such as potassium benzoate, flavoring agents and sweeteners. The preferred sweetener is aspartame as it demonstrates a synergistic effect with CaGP in providing a pleasant taste and mouth feel to the inventive beverage. Other natural and artificial sweeteners can be used, for example acesulfame K.

Typically, the beverage consists essentially of water; vitamin E, 10-18% by wt. calcium on a dry weight basis, said calcium is derived from calcium glycerophosphate; vitamin C; an acidulant mixture comprising 75% by wt. citric acid and 25% by wt. lactic acid; preservatives; sweeteners and flavoring agents; said beverage has a pH of about 3.1 to about 4.0 and provides at least 50% of the AI for calcium and at least 50% of the RDA for vitamin C, and at least 25% of the RDA for vitamin E for a pregnant or lactating woman in about 355 ml.

The liquid beverage concentrate of the invention may be prepared in a single vessel at ambient temperature by dissolving the ingredients in water using a blending tank equipped with vigorous agitation capability. Each ingredient should be completely dissolved before the next ingredient is added. In commercial beverage manufacturing, it is common for beverage concentrates to be prepared a day or more (often weeks or months) in advance of blending and filling containers with the final product. For this reason, the vitamin components should be added to the liquid beverage concentrate just prior to blending with water to complete the beverage in order to prevent unnecessary long term exposure to air.

Alternatively, a liquid dietary supplement in accordance with the invention may be carbonated by either blending the beverage concentrate with carbonated water or blending the beverage concentrate with water followed by carbonation of the blend. The beverage may be manufactured using a 5 to 1 ratio of beverage concentrate to non-carbonated water. Carbonation levels in the finished beverage may range from about 1.0-4.5 volumes of $CO_2$, depending on flavor or desired sensory attributes. The product is then packaged and sealed in aluminum cans or tinted glass bottles. During the production of the beverages, separate in-stream lines of beverage concentrate and water are combined in the proper ratio by a continuous metering device known in the art as a volumetric proportioner and then deaerated. The resulting mixture was transferred to a carbo-cooler where it was cooled and carbonated to approximately 2.5 volumes. The pH of the finished beverage should be in the range of about 3.1 to 4. The finished product is then filled into standard 12 oz. aluminum soda cans.

Pregnant and Lactating Women Nutritionals

Alternatively, the $\gamma$- to $\alpha$-tocopherol ratio of this invention may be added to a more complete nutritional supplement. The protein, fat and carbohydrate components described previously for the infant nutritional would typically be acceptable components for the adult nutritional. The adult nutritional formulas described herein may be used as a supplement to the diet or sole source of nutrition. The amount of calories and nutrients required will vary from person to person, dependent upon such variables as age, weight, and physiologic condition. The amount of nutritional formula needed to supply the appropriate amount of calories and nutrients may be determined by one of ordinary skill in the art, as may the appropriate amount of calorie and nutrients to incorporate into such formulas.

For example, an adult formula contains a protein component comprising from about 10 to about 80% of the total caloric content of said nutritional formula; a carbohydrate component comprising from about 10 to about 70% of the total caloric content of said nutritional formula; and a lipid component comprising from about 5 to about 50% of the total caloric content of said nutritional formula. The nutritional formula may be in liquid, powder or solid form.

Typically, one 8 oz. serving (285 calories) of the nutritional of the instant invention for a pregnant woman will comprise 8 gm of total fat (25% of calories), 17 gm of protein (23.8% of calories), 35 gm of carbohydrates (49% of calories) and at least 25% of the prenatal relevant amounts of vitamins and minerals.

Typically, one 8 oz. serving (225 calories) of the lactating woman nutritional of the instant invention will comprise 3 gm of total fat (12% of calories), 17 gm of protein (30% of calories), 32.5 gm of carbohydrates (58% of calories) and at least 25% of the lactating relevant amount of vitamins and minerals.

The liquid and powder nutritional supplement of this invention can be manufactured using techniques well known to those skilled in the art. Generally speaking an oil blend is prepared containing all oils, any emulsifier, and the fat-soluble vitamins. Two more slurries (carbohydrate and protein) are prepared separately by mixing the carbohydrate and minerals together and the protein in water. The two slurries are then mixed together with the oil blend. The resulting mixture is homogenized, heat processed, standardized with water-soluble vitamins. The concentrated final blend may be filed into appropriate packaging and sterilized; aseptically filed into sterile packaging; or dried and filed into appropriate packaging. The resulting powder may be milled to a specific particle size and/or aggolmerized to modify particle size and mixability characteristics. Those skilled in the nutritional formulation arts would also be able to dry blend the individual starting materials and add the liquid ingredients through agglomeration or during the dry blending step. The concentrate formula may also be diluted and filed into appropriate packaging and sterilized or aseptically filed into sterile packaging.

Numerous types of packaging are readily available and known to one practicing the art. Desirable packaging characteristics include: effective protection against impact, light, and heat; ease of opening; and efficient sealing for storage stability.

Using the recommendations of the FNB (Table 7) for pregnant and lactating women, one skilled in the art can readily calculate how much total vitamin E should be added to the nutritional product in the desired $\gamma$- to $\alpha$-tocopherol ratio of this invention. Practitioners also understand that appropriate additional amounts of the vitamin E ratio need be provided to compensate for some loss during processing and storage of such compositions.

Alternatively, a solid matrix nutritional of the instant invention comprises a protein source, a fat source, a carbohydrate source, vitamins, and minerals in amounts sufficient to supplement a pregnant or lactating woman's normal diet. Such amounts are well known by those skilled in the art and can be readily calculated when preparing such products.

For example, a solid matrix adult formula contains a protein component comprising from about 10 to about 80% of the total caloric content of said nutritional formula; a carbohydrate component comprising from about 10 to about 70% of the total caloric content of said nutritional formula; and a lipid component comprising from about 5 to about 50% of the total caloric content of said nutritional formula. The nutritional formula may be in liquid, powder or solid form.

Typically, one 60 gm bar (230 calories) of the nutritional of the instant invention for a pregnant woman will comprise 6 gm of total fat (24% of calories), 9 gm of protein (16% of calories), 35 gm of carbohydrates (60% of calories) and at least 25% of the prenatal relevant amounts of vitamins and minerals.

Typically, one 50 gm bar (220 calories) of the lactating woman nutritional of the instant invention will comprise 6 gm of total fat (24% of calories), 8 gm of protein (14% of calories), 34 gm of carbohydrates (62% of calories) and at least 25% of the lactating relevant amount of vitamins and minerals.

The solid matrix nutritional of the present invention will also desirably include a coating, flavoring and/or color to provide the nutritional products with an appealing appearance and an acceptable taste for oral consumption. For example, the nutritional bar of Example VII is coated with sugar free white confectionery coating. Examples of suitable coatings typically include compounded confectionery coating, milk chocolate coating, glazes, shellac, sugar free compounded confectionery coating, sugar free glazes and sugar free shellac. Examples of useful flavorings for the solid matrix nutritional typically include, for example, chocolate, butter pecan, strawberry, cherry, orange, peanut butter, graham and lemon.

The solid matrix nutritional of the instant invention will also desirably include ingredients, which add texture to enhance the mouth feel of the solid matrix nutritional. For example, crisp rice was added at about 6.4 wt/wt % of the nutritional bar in Example VII. Examples of other suitable ingredients, which can add texture typically, include nuts, soy nuggets, toasted oats, and fruit pieces.

The solid matrix nutritional compositions may be manufactured using cold extrusion technology as is known in the art. To prepare such compositions, typically all of the powdered components will be dry blended together. Such constituents typically include the proteins, vitamin premixes, certain carbohydrates, etc. The fat soluble components are then blended together and mixed with the powdered premix above. Finally any liquid components are then mixed into the composition, forming a plastic like composition or dough.

The process above is intended to give a plastic mass, which can then be shaped, without further physical or chemical changes occurring, by the procedure known as cold forming or extrusion. In this process, the plastic mass is forced at relatively low pressure through a die, which confers the desired shape, and the resultant exudate is then cut off at an appropriate position to give products of the desired weight.

The mass may, for example, be forced through a die of small cross-section to form a ribbon, which is carried on a belt moving at a predetermined speed under a guillotine type cutter which operates at regular intervals. The cutter, in this case, generally consists of a sharpened blade so adjusted that it cuts through the ribbon but not the underlying belt, but may also consist of a wire. In both cases, the principle is the same; the cutting process occurs at intervals that permit the moving ribbon to be cut into pieces of equivalent weight and dimensions. Generally, this is achieved by timing the cutting strokes and maintaining belt speed at an appropriate level, but there also exist computer controlled versions of this mechanism which offer greater versatility. Alternatively, the mass may be forced through a die of large cross-section and then cut at die level into slices by an oscillating knife or wire, which drop onto a moving belt and are thus transported away. The mass may also be extruded as a sheet, which is then cut with a stamp type cutter into shapes that are appropriate, such as a cookie type cutter. Finally, the mass may also be forced into chambers on a rotary die equipped with an eccentric cam that forces the thus-formed material out of the chamber at a certain point in a rotation of the cylindrical die.

After shaping, the formed product is moved by a transfer belt or other type of material conveyor to an area where it may be further processed or simply packaged. In general, a nutritional bar of the type described would be enrobed (coated) in a material that may be chocolate, a compound chocolate coating, or some other type of coating material. In all such cases, the coating material consists of a fat that is solid at room temperature, but that is liquid at temperature in excess of e.g. 31° C., together with other materials that confer the organoleptic attributes. The coating is thus applied to the bar while molten, by permitting the bar to pass through a falling curtain of liquid coating, at the same time passing over a plate or rollers which permit coating to be applied to the under surface of the bar, and excess coating is blown off by means of air jets. Finally, the enrobed bar passes through a cooling tunnel where refrigerated air currents remove heat and cause the coating to solidify.

Numerous types of packaging are readily available and known to one practicing the art. Desirable packaging characteristics include: effective protection against impact, light, and heat; ease of opening; and efficient sealing for storage stability.

Using the recommendations of the FNB (Table 7) for pregnant and lactating women, one skilled in the art can readily calculate how much total vitamin E should be added to the nutritional product in the desired γ- to α-tocopherol ratio of this invention. Practitioners also understand that appropriate additional amounts of the vitamin E ratio need be provided to compensate for some loss during processing and storage of such compositions.

The following non-limiting Examples will further illustrate the present invention.

CLINICAL EXAMPLE I

In adults, RRR-α-tocopheryl acetate (natural vitamin E) is preferentially utilized about twice as often when compared to all-rac-α-tocopheryl acetate (synthetic vitamin E) but similar studies have not been done in term infants. The objective of this study was to evaluate the vitamin E and antioxidant status of term infants fed formulas differing in the amount and type of vitamin E acetate stereoisomers.

Study Design and Procedures

A randomized, controlled, blinded, multi-site study was conducted to evaluate the effect of feeding infant formulas differing in the amount and type of vitamin E in term infants. Infants were in good health, full term at birth with a gestational age of 37 to 42 weeks, and a weight and length that were appropriate for gestational age (weight and length between the 5th and 95th NCHS percentiles). All infants had Apgar scores >5 at 1 minute, no signs of birth asphyxia, and showed no evidence of cardiac, gastrointestinal, or respiratory disease. Infants with any systemic disease or a family blood group incompatibility were excluded from the study. Infants in formula groups did not receive any breast milk. A parent or guardian agreed to provide the infant with the assigned study formula ad libitum as the sole source of nutrition for a minimum of 2 months. Water was given ad libitum as well.

Infants (116) were randomly assigned to one of the three study feedings between 0 and 8 days of life: (1) an Enfamil® formula (EF, Mead Johnson, Evansville, Ind.) containing 13.5 IU (or 13.5 mg) per liter of synthetic all-rac-α-tocopheryl acetate (13.5ALL group); (2) a Similac® with Iron (SWI, Ross Laboratories, Columbus, Ohio) formula containing 10 IU (or 7.3 mg) per liter of natural RRR-α-tocopheryl acetate (10RRR group); (3) an identical SWI formula but containing 20 IU (or 14.5 mg) per liter of natural RRR-α-tocopheryl acetate (20RRR group). Infants did not receive any vitamin or mineral supplementation except fluoride. The compositions of the three study formulas were very similar, i.e. 15 g/L protein, 36 g/L fat and 73 g/L carbohydrate. The EF formula contained 37% monounsaturated fatty acids, 20% polyunsaturated fatty acids, and 42.3% saturated fatty acids whereas the SWI formulas contained 40% monounsaturated fatty acids, 24% polyunsaturated fatty acids and 35% saturated fatty acids. The iron level in the EF formula was slightly lower (12.2 mg/L) than that in the SWI formulas (14.0 mg/L) All study formulas met or exceeded levels of nutrients as recommended by the committee on Nutrition of the American Academy of Pediatrics and required by the infant Formula Act.

An additional group (40 subjects) of human milk (HM)-fed infants was used as a reference group. Weight and length gains were recorded at 1 and 2 months of age and blood samples were obtained for the biochemical measurements detailed below. Formula consumption was recorded on the daily intake records by the parents for the 3 days preceding each study visit.

Isolation of Red Blood Cells and Plasma

Approximately 2 mL of blood was drawn into a vacutainer containing 3.6 mg K2EDTA and centrifuged at 2600 g for 15 min. Plasma (about 0.8 mL) was removed and 8 μL of propyl gallate (1 mg/mL) added as a preservative before the samples were frozen at −70° C. For red blood cells (RBCs) the buffy coat was removed and the remaining cells were washed two times with PBS, pH 7.4 buffer. The final RBC pellet was taken up in one volume of PBS buffer to give a 50% suspension (total volume of about 0.6 mL). A 6 μL aliquot of propyl gallate (1 mg/mL) was added to the RBC suspension. The RBC hematocrit was determined with a microcapillary centrifuge. The RBC suspension was stored at −70° C. Plasma and RBC vitamin E was measured as described below.

Plasma Tocopherols and α-Tocopheryl Quinone

Tocopherols (α-tocopherol and γ-tocopherol) and α-tocopheryl quinone were measured by a modification of the HPLC electrochemical detection technique described by Murphy et al (Journal of Chromatography 1987; 421:71-82) using a 3 micron, C18-reverse phase column (80×4.6 mm) and an ESA Coulochem II Model 5200A electrochemical detector (ESA, Chelmsford, Mass.). The reducing electrode was set to −600 mV (to reduce any tocopheryl quinone) and the downstream detection electrode set at 400 mV. In this method, the mobile phase was 20 mM ammonium acetate/1 μM EDTA in a solvent containing 90% methanol and 10% water (all HPLC grade). Tocol was used as an internal standard. A PE Nelson 900 Series analog-to-digital interface was used to acquire data that were then analyzed with the Turbochrom Chromatography Workshop Software installed in a Dell OptiPlex 133 MHZ Pentium Computer.

Red Blood Cell Tocopherols

RBC tocopherols were extracted and analyzed by the HPLC method used by Mino, et al. (American Journal of Clinical Nutrition 1985; 41:631-8) using ascorbate and pyrogallol as preservatives. Tocol was used as an internal standard. A reverse phase Altex-Ultrasphere-ODS (Beckman Instruments, Inc, Fullerton, Calif.) 4.6 mm ID×25 cm column was used and the tocopherols were eluted with a mobile phase consisting of methanol:water (99.5%:0.5%, vol:vol). A McPherson Model FL-750 spectrofluorescence detector (McPherson Instrument, Acton, Mass.) was utilized with 294 nm for excitation and 324 nm for emission.

Plasma Cholesterol and Triglyceride

Plasma cholesterol and triglycerides (TG) were enzymatically assayed using the Abbott Spectrum EPx Clinical Chemistry Analyze assays. This enabled the normalization of plasma tocopherol levels to lipids (cholesterol+TG) as suggested by van Zaeren-Grobben et al (Journal of Pediatric Gastroenterology and Nutrition 1998; 26:73-9).

Isoprostanes

Isoprostane levels in plasma were used to assess oxidative stress. A competitive enzyme immunoassay kit (Cat#516351) from Cayman Chemical Co. (Ann Arbor, Mich.) was used to determine levels of 8-epi-$PGF_{2\alpha}$ in plasma. The kit was used according to the manufacture's instructions.

Study Feedings

The study formulas were Enfamil® RTF and Similac® with iron RTF at two natural RRR-α-tocopheryl acetate levels. The Enfamil® was purchased commercially while the two Similac® with iron products were manufactured by the representative process described in Example II. The relevant nutrient compositions are shown in Table 10 below.

TABLE 10

Nutrient composition of study formulas

| Nutrient | Enfamil® | Similac® With Iron | Similac® With Iron |
|---|---|---|---|
| α-tocopheryl acetate, IU/L | 13.5 (13.5 mg/L) | 10 (7.3 mg/L) | 20 (14.5 mg/L) |
| form | all-rac- | RRR- | RRR- |
| Protein, g/L | 15 | 15 | 15 |
| Fat, g/L | 36 | 36 | 36 |
| Sources | palm olein oil, soy oil, coconut oil, high oleic sunflower oil | soy oil, coconut oil, high oleic safflower oil | soy oil, coconut oil, high oleic safflower oil |
| Carbohydrate, g/L | 73 | 73 | 73 |

Statistical Analysis

The hypothesis of no difference among the three feeding groups was tested using repeated measures analysis, which compared the feeding regimen groups over the entire study period. All tests were carried out using a 0.05 significance level. All statistical analyses were done for the three randomized groups; the data for the breastfed group are shown as reference data. Pearson's Chi-square or Fisher's exact test was used for categorical variables. Research sites were included as random blocks in the analyses.

A post-hoc analysis was done comparing only two groups using repeated measures analysis. The two groups, 10RRR and 13.5ALL were selected because the infants were fed different forms of vitamin E (natural vs synthetic); and the synthetic vitamin E group compared to the natural vitamin E group received approximately twice the amount of vitamin E (11.5 vs 6.0 mg/L, respectively). As part of the post-hoc analyses, a Discriminant Analysis was performed to identify significant variables that described the population. The F-test statistic was used in this analysis (25, 26, 27). Note that in a classification analysis the usual Type 1 error of 0.05 is not used; instead a pair of p-values for inclusion and exclusion is specified. In this analysis, the SAS software default values for performing a classification analysis were used. Also the human-milk reference group was included as part of the Discriminant analysis in order to compare the vitamin E and antioxidant profile of the HM group with the profiles of the other two groups using the biochemical indices identified as significant. For all practical purposes this analysis was used to determine which formula group as assessed by the derived discriminant functions was closes to the human milk group.

Results

Study Population

Thirty-seven infants were randomized to the 20RRR group, 40 infants were randomized to the 10RRR group, and 39 infants were randomized to the 13.5ALL group. Twenty-six, 25, and 26 infants adhered to the feeding protocol in each group, respectively. There were no differences between the groups in the number of infants who exited the study.

Entrance, Demographic, Anthropometric and Formula Intake Data

No differences were detected at entry between the 20RRR, 10RRR and 13.5All groups for gender or ethnicity. Gestational age at birth, birth weight, birth length and age at enrolment were not different among groups. No significant differences in formula intake were observed between the groups during the study. There was no difference in the vitamin E acetate intake between the 20RRR group (11.5±0.3 mg/day) and the 13.5ALL group (11.5±0.3 mg/day). The 10RRR group had a vitamin E acetate intake of 6.0±0.2 mg/day.

Vitamin E Status in Term Infants

There were consistent differences between the groups with respect to vitamin E status. The plasma α-tocopherol level (expressed as μmol/L of plasma) in the 20RRR group was significantly higher than in the 13.5ALL group during the study (LS Means: 31 vs 25 μmol, respectively, p=0.01). The total plasma lipid concentration (i.e., the sum of the plasma cholesterol and triglyceride levels) was used to normalize the plasma vitamin E levels. When plasma vitamin E was normalized, the plasma α-tocopherol/lipid ratio (expressed as μmol/mmol) in the 20RRR group was also significantly higher than the 10RRR and 13.5ALL groups (LS Means: 6.3 μmol/mmol vs 5.1 and 5.2 μmol/mmol, respectively, =p=0.005). RBC α-tocopherol levels were not different between groups. Surprisingly in the HM-fed reference group, the α-tocopherol levels in both plasma and RBCs were lower than the values observed for any of the formula-fed groups.

Significant differences were observed in γ-tocopherol levels, as well as γ-tocopherol/α-tocopherol ratio, between the different formula groups during the study. Infants fed the 10RRR formula had higher levels of plasma γ-tocopherol (expressed as μmol/L or μmol/mmol of lipids) than infants fed the 13.5ALL formula. In addition, the γ-tocopherol/α-tocopherol ratio in plasma was significantly higher in the 10RRR group as compared to the 20RRR and 13.5ALL groups (10RRR>13.5ALL, 20RRR, p=0.001). The γ-tocopherol/α-tocopherol ratios in RBC were significantly higher in both the 10RRR and 13.5ALL groups as compared to the 20RRR group (10RRR, 13.5ALL>20RRR, p=0.02).

Antioxidant Status in Term Infants

There were no statistically significant differences in antioxidant status between the three groups as assessed by the concentrations of isoprostanes (8-epi-FGF$_{2\alpha}$) or by vitamin E redox status (plasma α-tocopherol quinone/1-tocopherol). However, statistical significance was approached, showing a lower isoprostane level in the 10RRR group compared with the other groups (10RRR<20RRR, 13.5ALL; p<0.08). Moreover, when only two feeding groups, 10RRR and 13.5ALL, were compared, the 10RRR group had significantly lower plasma isoprostane levels (LS Means: 333 pg/mL vs 416 pg/mL, p=0.05).

The Discriminant analysis was used to identify which biochemical variables were meaningful and most sensitive in discerning the differences between the 10RRR and 13.5ALL groups, as part of a post-hoc analysis. The analysis identified four significant variables; plasma γ-tocopherol/α-tocopherol (p=0.000001), isoprostanes (p=0.019), vitamin E redox status (p=0.020) and plasma α-tocopherol/lipid (p=0.033) were important in predicting with which of the formula groups a particular infant was associated. The accuracy of classification of subjects into the correct group was 87.5%. Further, when the model classified the breastfed group, 77% (13 out of 17 subjects) were classified as the 10RRR group. It is interesting to note that both antioxidant parameters were important in classifying subjects into their respective groups.

Conclusions

The vitamin E status of infants in all three formula groups and the breastfed group were within normal reference ranges during the study. A plasma α-tocopherol level of 11.6 μmol/L is suggestive of vitamin E deficiency and a level greater than about 80 μmol/L is associated with toxicity. The mean plasma levels of α-tocopherol in infants in all three formula groups ranged from 25 μmol/L to 33 μmol/L. The breastfed group had somewhat lower mean plasma levels (18 to 20 μmol/L) as compared to the formula-fed groups. Additionally, the mean plasma α-tocopherol/lipid ratios in the three formula groups and the breastfed group were above 1.68 μmol/mmol, considered deficient in adults.

The breastfed group had very low RBC α-tocopherol levels (110-143 μg/dL) as compared to the formula-fed groups (230-288 μg/dL). The mean RBC α-tocopherol level in the breastfed group remained below the normal adult level of <200 μg/dL. This data suggests that the secretion of vitamin E into breast milk further discriminates between natural and synthetic vitamin E carried in plasma lipoproteins.

The 20RRR and 10RRR formulas contained approximately the same level of γ-tocopherol, which is derived from the vegetable oils that were the same in both formulas. Although the concentrations of γ-tocopherol in the two formulas were similar, the 10RRR group had a higher concentration of γ-tocopherol in all parameters measured (plasma, plasma/lipid ratio, and RBC) than the 20RRR group during the study. Although this was not statistically significant, the lower concentration of γ-tocopherol in the 20RRR group may be attributed to the higher intake of RRR-α-tocopherol in this group.

This is the first study to suggest that infants discriminate between RRR-α-tocopherol (natural vitamin E) and the other seven stereoisomers present in synthetic vitamin E. The 10RRR formula with 7.3 mg RRR-α-tocopherol/L performed as well or better on all vitamin E and antioxidant parameters as the 13.5 RRR formula with 13.5 mg/L of synthetic vitamin E. Vitamin E status in all three feeding groups was within normal reference ranges during the study. The results also suggest that when infants are fed the higher-containing natural vitamin E formula (20RRR), blood levels of γ-tocopherol may be suppressed. An infant formula containing 10 IU of natural vitamin E promotes adequate vitamin E status.

The findings in this study relative to antioxidant study were unexpected. The hypothesis at the beginning of the study was that infants fed the product containing the higher dose of natural vitamin E would have better antioxidant status; however, this was not the case. Infants fed the product containing the lower dose of natural vitamin E showed a trend toward better antioxidant status as measured by plasma isoprostanes (p=0.08). Further, when only two feeding groups, 10RRR (7.3 mg/dL natural vitamin E) and 13.5ALL (13.5 mg/dL synthetic vitamin E), were compared, statistical significance was reached in which the 10RRR group had a lower concentration of plasma isoprostanes. Isoprostanes are formed in vivo by the free radical oxidation of arachidonyl-containing lipids and lower plasma levels of isoprostanes suggest better antioxidant status. Note that none of the three formulas studied contained long-chain polyunsaturated fatty acids (LC-PUFAs), thus, the isoprostanes levels observed in these groups would not have been affected by diet. However, HM contains arachidonic acid, which may have contributed to the somewhat higher levels of isoprostanes observed in the breastfed group.

EXAMPLE II

As discussed above, the γ- to α-tocopherol ratio of this invention may be incorporated into infant nutritional formulas.

Table 11 presents a bill of materials for manufacturing 454 kg of a RTF infant nutritional. A detailed description of its manufacture follows.

TABLE 11

Bill of materials (454 kg)

| Ingredient | Amount |
| --- | --- |
| Ingredient water | 366 kg |
| High-oleic safflower oil | 6.3 kg |
| Coconut oil | 4.7 kg |
| Soybean oil | 4.7 kg |
| Lecithin | 162 gm |
| OSV premix | 20.3 gm |
| 30% Beta carotene | 0.734 gm |
| Vitamin A | 0.352 gm |
| Myverol | 162 gm |
| Carrageenan | 136 gm |
| Whey protein concentrate | 2.9 kg |
| Calcium carbonate | 227 gm |
| Magnesium chloride | 45.4 gm |
| Potassium citrate | 277 gm |
| Potassium chloride | 68 gm |
| Choline chloride | 24.5 gm |
| Lactose | 26.7 kg |
| Cond. Skim milk | 41 kg |
| ferrous sulfate | 7.2 gm |
| WSV/mineral premix | 64.8 gm |
| Riboflavin | 1.12 gm |
| Nucleotide/choline premix | 133 gm |
| Ascorbic acid | 178 gm |

OSV premix(per g premix): 69,000 IU/g vitamin A, 10,650 IU/g vitamin D$_3$, 275 IU/g vitamin E (RRR-α-tocopherol acetate), 2.20 mg/g vitamin K$_1$
WSV premix(per g premix): 65 mg/g niacinamide, 39 mg/g calcium pantothenate, 1.8 gm/g folic acid, 10 mg/g thiamine chloride hydrochloride, 6.9 gm/g riboflavin, 3.4 mg/g pyridoxine hydrochloride, 31.5 mg/g cyanocobalamin, 0.395 mg/g biotin, 11.25 mg/g iron, 37 mg/g zinc, 4.78 mg/g copper, 0.3785 mg/g manganese, 98 mcg/g selenium, 305 mg/g taurine, 222 mg/g m-inositol A protein-in-fat blend is prepared by heating the specified amount of high-oleic safflower oil, coconut oil and soy oil to 54° C.-60° C. with agitation. The emulsifiers (Centrol CA a standard fluid lecithin distributed by Central Soya, Ft. Wayne, Ind.; and Myverol 18-06 is distilled monoglycerides) are then added under agitation and allowed to dissolve. The oil soluble vitamin premix, vitamin A and beta-carotene (distributed by Vitamins, Inc., Chicago, Ill.) are added to the oil blend with agitation. The carrageenan is added. With agitation, the required amount of whey protein concentrate (AMP 800 distributed by AMPC, Inc. Ames, Iowa) is added. Once all the protein is in solution the required amount of calcium carbonate is added and dissolved completely. The completed oil slurry is held under moderate agitation at a temperature from 26° C. to 48° C. for a period of no longer than six hours until it is blended with the other slurry.

The final blend is prepared by heating the ingredient water to 68° C.-74° C. With agitation, the specified amounts of magnesium chloride, potassium citrate, potassium chloride, and choline chloride are added to the heated water. The slurry is agitated until the minerals are dispersed well and dissolved. The required amount of lactose is added with agitation. All of the protein-in-water slurry is added followed by the required amount of condensed skim milk. The slurry is held under agitation at 54° C.-60° C. for not longer than six hours until it is blended with the other slurries.

After waiting for at least five minutes with agitation the final blend pH is adjusted with 1N KOH to a pH from 6.45 to 6.60. The final blend is held for no longer than two hours after the pH check.

After waiting for a period of not less than five minutes or greater than two hours, the blend is subjected to deaeration, ultra high temperature heat treatment, and homogenization, as follows: deaerate the blend at 10-15 inches Hg; pass the blend through a plate/coil heater and heat the mix to 71° C. to 82° C.; emulsify the blend at 900-1100 psig in a single stage homogenizer; UHT process: Preheat the mix to 98-105° C., Heat mix by steam injection to 143-147° C. and hold for 5 seconds, Flash cool to 98-1-5° C., From the flash cooler, pass the mix through a plate cooler to further reduce the temperature to 74-70° C.; homogenize the blend at 3900 to 4100/400 to 600 psig in a two-stage homogenizer; and hold the mix at 74-82° C. for 16 seconds, cool the blend to a temperature from 1° C. to 7° C.; and store the blend at a temperature from 1° C. to 7° C.

After the above steps have been completed, appropriate analytical testing for quality control is conducted. Based on the analytical results of the quality control tests, batch corrections are made if need be.

The ascorbic acid solution is prepared by adding the required amount of 45% KOH to the 10° C. to 37° C. water with agitation. The required amount of ascorbic acid is added.

The vitamin/mineral solution is prepared by heating the ingredient water to 43° C. to 60° C. Under agitation, add the required amount of ferrous sulfate and let dissolve until the solution is a clear green. Add the water-soluble vitamin premix, riboflavin and the nucleotide/choline premix to the clear green solution. The solution is maintained at 43-54° C. with constant agitation.

All of the ascorbic acid solution and vitamin/mineral solution is then added to the blended slurry under agitation. The processed mix is held at moderate agitation until being filed into desired containers and terminally retorted.

EXAMPLE III

A batch of powder infant formula is manufactured as described in Example II except that the processed mix is sent to a spray dryer as described below.

The processed mix is preheated through a plate heater to 71° C.-82° C. before going to a surge tank. The mix leaves the surge tank and passes through the steam injector where it is heated to 88° C.-93° C. The mix enters the vapor-flash chamber where it is cooled to 71° C.-82° C., then pumped through an in-line 200 micro filter prior to the high-pressure pump and into the dryer. The dryer settings are as follows: the nozzle pressure 3000-5000 psig, the liquid flow rate 11 gpm max, the ingoing air temperature 160° C.-207° C., and outgoing air temperature 82° C.-108° C.

To control bulk density, dispersibility, particle size, moisture and physical stability, the specific spray nozzle, nozzle pressure, drying temperatures and fine reinjection parameters may vary depending upon the drying conditions of the day. The powder passes from the dryer into the powder cooler where the powder is cooled to below 43° C. The cooled powder is stored in appropriate containers until being filed into the desired packaging.

EXAMPLE IV

As discussed above, the $\gamma$- to $\alpha$-tocopherol ratio of this invention may be incorporated into a human milk fortifier powder, which is added to human milk.

A batch of fortifier powder is manufactured by combining the appropriate ingredients to generate one carbohydrate/mineral (CHO/MIN) slurry, one oil blend and one protein in water slurry (PIW). The CHO/MIN, oil blend and PIW slurries are mixed together to form the final blend. The final blend is then processed with an HTST treatment. After standardization, the final blend is spray dried.

Table 12 presents a bill of materials for manufacturing 8,172 kg of powdered human milk fortifier. A detailed description of its manufacture follows.

TABLE 12

Bill of materials

| Ingredient | Amount |
|---|---|
| Ingredient water | 16,205 L |
| Corn syrup solids | 1603 kg |
| Magnesium chloride | 96.2 kg |
| Potassium citrate | 223.8 kg |
| Sodium citrate | 6.6 kg |
| Sodium chloride | 15.4 kg |
| MCT oil | 801 kg |
| Lecithin | 16.6 kg |
| Vitamin A | 2.36 kg |
| Vitamin D | 359.3 g |
| Vitamin K | 27.5 g |
| RRR-$\alpha$-tocopherol acetate | 7.6 kg |
| RRR-$\gamma$-tocopherol acetate | 8.2 kg |
| Calcium carbonate | 33.1 kg |
| Tricalcium phosphate | 646 kg |
| Whey protein concentrate | 1506 kg |
| Non fat dry milk | 3307 kg |
| potassium citrate | 257.2 g |
| ferrous sulfate | 3.7 kg |
| Zinc sulfate | 11.1 kg |
| Copper sulfate | 1.84 kg |
| Manganese sulfate | 0.320 kg |
| Sodium selenate | 0.001 kg |
| Niacinamide | 0.98 kg |
| Riboflavin | 1.14 kg |
| Calcium pantothenate | 4.08 kg |
| Pyridoxine hydrochloride | 0.655 kg |
| m-inositol | 9.55 kg |
| Biotin | 0.0727 kg |
| Folic acid | 0.0775 kg |
| Cyanocobalamin | 0.0016 kg |
| Ascorbic acid | 153.5 kg |

A carbohydrate/mineral slurry is prepared by heating 2,763 liters of ingredient water to 54° C.-62° C. With agitation, the specified amounts of corn syrup solids (Maltrin M200 distributed by Grain Processing Corporation, Muscatine, Iowa), magnesium chloride, sodium chloride, sodium citrate, potassium citrate, ultra micronized tricalcium phosphate and calcium carbonate are added to the heated water. The slurry is held under agitation at 54° C.-62° C. for not longer than six hours until it is blended with the other slurries.

An oil blend is prepared by heating the specified amount of MCT oil (distributed by Stepan, Maywood, N.J.) to 32° C.-37° C. with agitation. An emulsifier (standard fluid lecithin distributed by Central Soya, Ft. Wayne, Ind.) is then added under agitation and allowed to dissolve. Vitamin A, D, K and Vitamin E (distributed by Vitamins, Inc., Chicago, Ill.) are then added to the slurry with agitation. The completed oil slurry is held under moderate agitation at a temperature from 26° C. to 48° C. for a period of no longer than six hours until it is blended with the other slurries.

A protein-in-water slurry is prepared by heating 9,053 liters of ingredient water to 48° C.-60° C. With agitation, the specified amount of whey protein concentrate (AMP 800 distributed by AMPC, Inc. Ames, Iowa) and nonfat dry milk is added to the heated water. The completed protein-in-water slurry is not held but blended directly with the other slurries.

The protein-in-water, oil blend and carbohydrate/mineral slurries are blended together with agitation and the resultant blend is maintained at a temperature from 51° C. to 60° C. After waiting for at least five minutes with agitation the final blend pH is adjusted with 1N KOH to a pH from 6.45 to 6.80. The total solids of the final blend is 30%. The final blend is held for no longer than two hours after the pH check.

After waiting for a period of not less than five minutes nor greater than two hours, the blend is subjected to deaeration, high-temperature-short-time heat treatment, and homogenization, as follows: deaerate the blend at 10-15 inches Hg; emulsify the blend at 900-1100 psig in a single stage homogenizer; pass the blend through a plate/coil heater and heat the mix to 71° C. to 82° C.; homogenize the blend at 3900 to 4100/400 to 600 psig in a double stage homogenizer; pass the blend through a 16 second hold tube at a temperature from 73° C. to 85° C.; cool the blend to a temperature from 1° C. to 7° C.; and store the blend at a temperature from 1° C. to 7° C.

After the above steps have been completed, appropriate analytical testing for quality control is conducted. Based on the analytical results of the quality control tests, batch corrections are made if need be. Final blend total solids are from 29% to 31%.

A water soluble vitamin solution, ascorbic acid solution and trace mineral solution are prepared separately and added to the processed blend.

The ascorbic acid solution is prepared by adding the required amount of ascorbic acid to 2,453 liters of 10° C. to 37° C. water with agitation.

The mineral solution is prepared by heating 321 liters of ingredient water to 37° C. to 65° C. Under agitation, add the required amount of potassium citrate and ferrous sulfate. Allow to agitate until the solution is a clear green color. Add the required amounts of zinc sulfate, copper sulfate, manganese sulfate and sodium selenate to the green mineral solution. Agitate five minutes minimum.

The water soluble vitamin solution is prepared by heating 530 liters of ingredient water to 37° C. to 65° C. The required quantities of niacinamide, riboflavin, calcium pantothenate, pyridoxine hydrochloride, thiamine hydrochloride, m-insitol, biotin, folic acid and cyanocobalamin are added to the heated water.

All of the ascorbic acid solution, the mineral solution and water soluble vitamin solution is then added to the blended slurry under agitation.

The final mix is preheated through a plate heater to 71° C.-82° C. before going to a surge tank. The mix leaves the surge tank and passes through the steam injector where it is heated to 88° C.-93° C. The mix enters the vapor-flash chamber where it is cooled to 71° C.-82° C., then pumped through an in-line 200 micro filter prior to the high pressure pump and into the dryer. The dryer settings are as follows: the nozzle pressure of 3000-5000 psig, the liquid flow rate at 11 gpm max, the ingoing air temperature at 160° C.-207° C., and the outgoing air temperature at 82° C.-108° C.

To control bulk density, dispersibility, particle size, moisture and physical stability, the specific spray nozzle, nozzle pressure, drying temperatures and fine reinjection parameters may vary depending upon the drying conditions of the day. The powder passes from the dryer into the powder cooler where the powder is cooled to below 43° C. The cooled powder is stored in appropriate containers until being filed in individual packets.

EXAMPLE V

As discussed above, the γ- to α-tocopherol ratio of this invention may be incorporated into adult nutritionals.

Table 13 presents a bill of materials for manufacturing 1,000 kg of a typical vanilla flavored liquid nutritional product. A detailed description of its manufacture follows.

TABLE 13

| Bill of Materials for Vanilla Liquid Nutritional | |
|---|---|
| Ingredient | Quantity per 1,000 kg |
| Water | QS |
| Corn Syrup | 33 kg |
| Maltodextrin | 28 kg |
| Sucrose | 19.4 kg |
| Caseinate | 8.7 kg |
| High Oleic Safflower Oil | 4.1 kg |
| Canola Oil | 4.1 kg |
| Soy Protein | 3.7 kg |
| Whey Protein | 3.2 kg |
| Caseinate | 2.9 kg |
| Corn Oil | 2.0 kg |
| Tricalcium Phosphate | 1.4 kg |
| Potassium Citrate | 1.3 kg |
| Magnesium Phosphate | 952 gm |
| Lecithin | 658 gm |
| Magnesium chloride | 558 gm |
| Vanilla Flavor | 544 gm |
| Sodium Chloride | 272 gm |
| Carrageenan | 227 gm |
| Choline chloride | 218 gm |
| UTM/TM Premix | 165 gm |
| Potassium Chloride | 146 gm |
| Ascorbic Acid | 145 gm |
| Sodium Citrate | 119 gm |
| Potassium Hydroxide | 104 gm |
| Lutein (5%) | 46 gm |
| WSV Premix | 33 gm |
| Vit DEK Premix | 29 gm |
| Vitamin A | 3.7 gm |
| RRR-γ-tocopherol acetate | 20.3 gm |
| Potassium Iodide | 86 mcg |

WSV premix(per g premix): 375 mg/g niacinamide, 242 mg/g calcium pantothenate, 8.4 gm/g folic acid, 62 mg/g thiamine chloride hydrochloride, 48.4 gm/g riboflavin, 59.6 mg/g pyridoxine hydrochloride, 165 mcg/g cyanocobalamin and 7305 mcg/g biotin
Vitamin DEK premix(per g premix): 8130 IU/g vitamin $D_3$, 838 IU/g vitamin E(RRR-α-tocopherol acetate), 1.42 mg/g vitamin $K_1$
UTM/TM premix(per g premix): 45.6 mg/g zinc, 54 mg/g iron, 15.7 manganese, 6.39 mg/g copper, 222 mcg/g selenium, 301 mcg/g chromium and 480 mcg/g molybdenium The liquid nutritional products of the present invention are manufactured by preparing three slurries that are blended together, heat treated, standardized, packaged and sterilized.

A carbohydrate/mineral slurry is prepared by first heating the required amount of water to a temperature of from about 65° C. to about 71° C. with agitation. With agitation, the required amount of potassium citrate and ultra trace mineral/trace mineral (UTM/TM) premix (distributed by Fortitech, Schnectady, N.Y.) is added. The slurry is greenish yellow in color. Agitation is maintained until the minerals are completely dispersed. With agitation, the required amounts of the following minerals are then added: magnesium chloride, potassium chloride, sodium chloride, sodium citrate, potassium iodide, magnesium phosphate and tricalcium phosphate. Next, the maltodextrin distributed by Grain Processing Corporation, Muscataine, Iowa, U.S.A., sucrose and corn syrup are added to slurry under high agitation, and are allowed to dissolve. The completed carbohydrate/mineral slurry is held with agitation at a temperature from about 65° C. to about 71° C. for not longer than eight hours until it is blended with the other slurries.

A protein in fat slurry (PIF) is prepared by combining and heating the required amounts of high oleic safflower oil and canola oil to a temperature from about 40.5° C. to about 49° C. with agitation. With agitation, the required amounts of free lutein from Kemin Foods of Des Moines, Iowa is added. Agitate for a minimum of 15 minutes. Add the following ingredients are added to the heated oil: lecithin (distributed by Central Soya Company, Fort Wayne, Ind.), vitamin A, RRR-γ-tocopherol acetate, and Vitamin D, E, K premix (distributed by Vitamins Inc., Chicago, Ill.). The required amount of carrageenan is dry blended with the required amount of whey protein and add to the agitating lipid mixture and allowed to agitate for a minimum of 10 minutes. The required amount of soy protein is added to the blend slowly to assure proper mixing. The completed oil/protein slurry is held under moderate agitation at a temperature from about 40° C. to about 43° C. for a period of no longer than two hours until it is blended with the other slurries.

A protein in water slurry is prepared by first heating about required amount of water to a temperature of about 40° C. with agitation. The caseinate is added and the slurry is agitated well until the caseinate is completely dispersed. With continued agitation, the slurry is slowly warmed to 60° C. to 65° C. The slurry is held for no longer than twelve hours until it is blended with the other slurries.

The batch is assembled by blending required amount of protein slurry with required amount of the carbohydrate/mineral slurry and allowed to agitate for 10 minutes. With agitation, the required amount of the oil/protein slurry is added and agitate for at least 10 minutes. The pH of the blended batch is adjusted to a pH of 6.66 to 6.75 with 1N potassium hydroxide.

After waiting for a period of not less than one minute nor greater than two hours, the blend slurry is subjected to deaeration, ultra-high-temperature treatment, and homogenization. The blended slurry is heated to a temperature from about 71° C. to about 82° C. and deareated under vacuum. The heated slurry is then emulsified through a single stage homogenizer at 900 to 1100 psig. After emulsification, the slurry is heated from about 99° C. to about 110° C. and then heated to a temperature of about 146° C. for about 5 seconds. The slurry is passed through a flash cooler to reduce the temperature to from about 99° C. to about 110° C. and then through a plate cooler to reduce the temperature to from about 71° C. to about 76° C. The slurry is then homogenized at 3900 to 4100/400 to 600 psig. The slurry is held at about 74° C. to about 80° C. for 16 seconds and then cooled to 1° C. to about 7° C. At this point, samples are taken for microbiological and analytical testing. The mixture is held under agitation.

A water soluble vitamin (WSV) solution is prepared separately and added to the processed blended slurry.

The vitamin solution is prepared by adding the following ingredients to 9.4 kg of water with agitation: WSV premix (distributed by J.B. Laboratories, Holland, Mich.), vitamin C, choline chloride, L-carnitine, taurine, inositiol, folic acid, pyridoxine hydrochloride and cyanocobalamin. The required amount of 45% potassium hydroxide slurry is added to bring the pH to between 7 and 10.

Based on the analytical results of the quality control tests, an appropriate amount of water is added to the batch with agitation to achieve the desired total solids. Additionally, 8.8 kg of vitamin solution is added to the diluted batch under agitation.

The product pH may be adjusted to achieve optimal product stability. The completed product is then placed in suitable containers and subjected to terminal sterilization.

EXAMPLE VI

The process for manufacturing 1 Kg of a lemon flavored nutritional bar of the instant invention, using the bill of materials from Table 14 is described in detail below.

TABLE 14

Listing of ingredients for lemon flavored nutritional bar

| Ingredient | Quantity per 1 kg |
|---|---|
| Sugar free white confectionery coating | 190 gm |
| Soy protein | 162.3 gm |
| Honey | 143.5 gm |
| Fibersol 2(E) | 107.9 gm |
| High fructose corn syrup | 91.5 gm |
| rice crisps | 63.5 gm |
| Soy polysaccharide | 49.1 gm |
| Glycerin | 46.3 gm |
| vit/min premix | 28.2 gm |
| high oleic safflower | 27.9 gm |
| fructooligosaccharide | 21.2 gm |
| encapsulated guar gum | 16.5 gm |
| microcrystalline cellulose | 13.3 gm |
| Canola | 11.7 gm |
| NA lemon creme | 10.1 gm |
| Fructose | 7.8 gm |
| citric acid | 3.3 gm |
| m-inositol | 2.9 gm |
| soy lecithin | 2.8 gm |
| RRR-γ-tocopherol acetate | 911 mg | vit/min premix(per g premix): 1219 IU vitamin A, 90 IU vitamin $D_3$, 38 IU vitamin E(RRR-α-tocopherol acetate), 19.8 mcg vitamin $K_1$, 90 mg vitamin C, 4.9 mg niacinamide, 2.33 mg calcium pantothenate, 0.187 mg folic acid, 0.377 mg thiamine mononitrate, 0.645 mg riboflavin, 0.457 mg pyridoxine hydrochloride, 2.91 mcg cyanocobalamin, 74.65 mg biotin, 2.77 mg zinc, 3.3 mg iron, 0.797 mg manganese, 0.33 mg copper, 35.1 mcg iodine, 35.9 mcg chromium, 24.3 mcg molybdenum, 24.6 mcg selenate, 227 mg calcium, 56.5 gm magnesium and 120.3 mg phosphorous The bar core is prepared by mixing a dry preblend in two stages, adding the liquid preblend followed by the canola oil. A dry preblend is prepared by mixing the required amounts of soy protein (distributed by Protein Technologies International, St. Louis, Mo.), fructooligosaccharide (distributed by Golden Technologies Company of Golden, Colo.), m-inositol and soy polysaccharide (distributed by Protein Technologies International, Louis, Mo. under the name of Fibrim 1450) for 10 minutes in a Ribbon Blender. The required amounts of the following ingredients are added to the Ribbon Blender: microcrystalline cellulose, citric acid and Fibersol 2(E) (distributed by Matsutani Chemical Industry Co., Hyogo, Japan) and mixed for an additional 20 minutes. 25 kg of the blend is removed from the bottom of the blender and added back through the top of blender and mixed for an additional 5 minutes. The dry preblend is stored in drums.

The required amount of the dry preblend above is added to a Dough Mixer along with the required amounts of lemon creme flavor (distributed by Givaudan Roure, Cincinnati, Ohio under the name of NA Lemon Creme), vit/min premix (distributed by Fortitech, Schenectady, N.Y.), RRR-γ-tocopherol acetate, microencapsulated guar gum (distributed by Coating Place, Verona, Wis.) and rice crisp (distributed by Weetabix, Clinton, Mass. under the name of Densifeid Crisp Rice-No sugar, salt or malt) and mixed for 200 strokes by the Dough Mixer.

The liquid preblend is prepared by adding the required amount of high fructose corn syrup (distributed by ADM Corn Processing, location under the name of cornsweet 95), honey, glycerine, crystalline fructose, high oleic safflower oil (distributed by California Oils, Richmond, Calif.) and bleached lecithin in a Hobart Mixer for 5 minutes.

All of the liquid preblend is added to the dry preblend in the Dough Mixer within the first 60 strokes. The total mixing time is set for 500 strokes. When 100 to 150 strokes is remaining, the required amount of canola oil is added to the Dough Mixer.

The mixed material is transferred from the Dough Mixer to the extruder. The extruder is adjusted to produce bar cores from 33.3 gm to 37.3 gm, the target weight is set at 35.3 gm. The extruded bar cores are conveyed through the cooling tunnel set at the target range of 8 to 12° C.

The bar cores are coated with a maltitol white confectionery coating prepared as follows. The coating is melted at a temperature range between 46-48° C. The temperature is not allowed to exceed 50° C. in the melter. Once melted, the coating is held between 46-48° C. for 30 minutes to insure destruction of all unstable crystal.

The extruded bar cores are conveyed through the enrober. The coating is applied to the bars at a temperature range between 41-48° C. The coating temperature is not allowed to exceed 50° C. in the enrober. The target percent coating is 16.3%, 19% is the maximum coating percent.

After the enrober, the coated bars are conveyed through the cooling tunnel set at 10° C., the cooling range is from 8-13° C. The bars pass through a metal detector prior to wrapping. The cooled bars are packaged in foil wrap.

We claim:

1. A method of improving the antioxidant status of an infant, said method comprising the steps of
   (A) preparing an infant formula comprising fat, protein, carbohydrate, minerals, and natural tocopherols, said fat including oils comprising RRR-γ-tocopherol and RRR-α-tocopherol,
   (B) adding to the prepared formula additional tocopherols consisting essentially of isolated RRR-γ-tocopherol, isolated RRR-α-tocopherol, or both, to achieve a weight ratio of RRR-γ-tocopherol to RRR-α-tocopherol in the infant formula of from 1:2 to about 6:1, and
   (C) administering the formula to an infant.

2. The method of claim 1, wherein the infant formula comprises:
   (A) from about 6% to about 25% protein as a percentage of total calories,
   (B) from about 35% to about 50% carbohydrate as a percentage of total calories,
   (c) from about 30% to about 50% lipid as a percentage of total calories.

3. The method of claim 1 wherein the infant formula is administered to a preterm infant.

4. A method of improving the antioxidant status of newborn infants, said method comprising the steps of
   (A) preparing a nutritional comprising fat, protein, carbohydrate, minerals, and natural tocopherols, said fat including oils comprising RRR-γ-tocopherol and RRR-α-tocopherol,
   (B) adding to the prepared nutritional additional tocopherols consisting essentially of isolated RRR-γ-tocopherol, isolated RRR-α-tocopherol, or both, to achieve a weight ratio of RRR-γ-tocopherol to RRR-α-tocopherol in the nutritional of from 1:2 to about 6:1, and
   (C) administering the nutritional to pregnant women.

5. The method of claim 4 wherein the weight ratio of RRR-γ-tocopherol to RRR-α-tocopherol ranges from about 1:1.4 to about 2:1.

6. A method of improving the antioxidant status of breast fed infants, said method comprising the steps of
   (A) preparing a nutritional comprising fat, protein, carbohydrate, minerals, and natural tocopherols, said fat including oils comprising RRR-γ-tocopherol and RRR-α-tocopherol,
   (B) adding to the prepared nutritional additional tocopherols consisting essentially of isolated RRR-γ-tocopherol, isolated RRR-α-tocopherol, or both, to achieve a weight ratio of RRR-γ-tocopherol to RRR-α-tocopherol in the nutritional of from 1:2 to about 6:1, and
   (C) administering the nutritional to lactating women.

7. The method of claim 6 wherein the weight ratio of RRR-γ-tocopherol to RRR-α-tocopherol ranges from about 1:1.4 to about 2:1.

* * * * *